United States Patent
Sosnowski et al.

(10) Patent No.: US 6,753,148 B2
(45) Date of Patent: *Jun. 22, 2004

(54) METHODS AND APPARATUS FOR DETECTING VARIANTS UTILIZING BASE STACKING

(75) Inventors: Ronald G. Sosnowski, Coronado, CA (US); Eugene Tu, San Diego, CA (US)

(73) Assignee: Nanogen, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/108,280

(22) Filed: Mar. 25, 2002

(65) Prior Publication Data

US 2002/0115098 A1 Aug. 22, 2002

Related U.S. Application Data

(63) Continuation of application No. 09/645,757, filed on Aug. 24, 2000, now Pat. No. 6,395,493, which is a continuation of application No. 09/030,156, filed on Feb. 25, 1998, now Pat. No. 6,207,373.

(51) Int. Cl.[7] .......................... C12Q 1/68; C12P 19/34; C12M 1/34; C07H 21/02; C07H 21/04

(52) U.S. Cl. .......................... 435/6; 435/7.1; 435/91.1; 435/91.2; 435/287.2; 530/22.1; 530/23.1; 530/24.3; 530/24.31; 530/24.32; 530/24.33

(58) Field of Search ........................... 435/6, 7.1, 91.1, 435/91.2, 287.2; 536/22.1, 23.1, 24.3, 24.31–33, 25.32

(56) References Cited

U.S. PATENT DOCUMENTS 4,963,663 A 10/1990 White et al.
5,324,631 A 6/1994 Helentjaris et al.

(List continued on next page.)

FOREIGN PATENT DOCUMENTS

| EP | 0 370 719 | 11/1989 |
|---|---|---|
| GB | 2 224 573 | 10/1989 |
| WO | WO90/04040 | 4/1990 |
| WO | WO 95/12808 A1 | 5/1995 |
| WO | WO95/30774 | 11/1995 |
| WO | WO96/31622 | 10/1996 |
| WO | WO 96/31622 | * 10/1996 |
| WO | WO96/36731 | 11/1996 |

OTHER PUBLICATIONS

Biomek Workstation 2000 see http://134.217.3.35/bekcman/biorsrch/prodinfo/biomek/biowork.asp.

(List continued on next page.)

Primary Examiner—Jeffrey Siew
(74) Attorney, Agent, or Firm—O'Melveny & Myers LLP

(57) ABSTRACT

Methods and apparatus are provided for the analysis and determination of the nature of repeat units in a genetic target. In one method of this invention, the nature of the repeat units in the genetic target is determined by the steps of providing a plurality of hybridization complex assays arrayed on a plurality of test sites, where the hybridization complex assay includes at least a nucleic acid target containing a simple repetitive DNA sequence, a capture probe having a first unique flanking sequence and n repeat units, where $n=0,1,2\ldots$, or fractions thereof, being complementary to the target sequence, and a reporter probe having a selected sequence complementary to the same target sequence strand wherein the selected sequence of the reporter includes a second unique flanking sequence and m repeat units, where $m=0,1,2\ldots$, or fractions thereof, but where the sum of repeat units in the capture probe plus reporter probe is greater than 0 ($n+m>0$). Concordance and discordance among the hybridization complex assays at the test sites is determined at least in part by hybridization stability. Electronic stringency control may be utilized. Applications include paternity testing, forensic use, and disease diagnostics, such as for the identification of the existence of a clonal tumor.

92 Claims, 21 Drawing Sheets

U.S. PATENT DOCUMENTS

| | | | |
|---|---|---|---|
| 5,354,855 A | 10/1994 | Cech et al. | |
| 5,364,759 A | 11/1994 | Caskey et al. | |
| 5,403,708 A | 4/1995 | Brennan et al. | |
| 5,605,662 A | 2/1997 | Heller et al. | |
| 5,632,957 A | 5/1997 | Heller et al. | |
| 5,753,439 A | 5/1998 | Smith et al. | |
| 5,759,773 A | 6/1998 | Tyagi et al. | |
| 5,795,716 A | 8/1998 | Chee et al. | |
| 5,849,486 A | 12/1998 | Heller et al. | |
| 5,881,269 A | 3/1999 | Dobbelstein | |
| 5,908,745 A | 6/1999 | Mirzabekov et al. | |
| 6,017,696 A | 1/2000 | Heller et al. | |
| 6,048,690 A | 4/2000 | Heller et al. | |
| 6,051,380 A | 4/2000 | Sosnowski et al. | |
| 6,090,549 A | 7/2000 | Mirzabekov et al. | |
| 6,150,097 A * | 11/2000 | Tyagi et al. ............... | 435/6 |
| 6,207,373 B1 * | 3/2001 | Sosnowski et al. ........... | 435/6 |
| 6,395,493 B1 * | 5/2002 | Sosnowski et al. ........... | 435/6 |

OTHER PUBLICATIONS

Chen, E.C.M. et al., "The Role of Electron Donors and Acceptors in Base Stacking in DNA and RNA", Biochemical and Biophysical Research Communications, vol. 171, No. 1, pp 97–101, Aug. 31, 1990.

Friedman, Richard A. et al., "A Free Energy Analysis of Nucleic Acid Base Stacking in Aqueous Solution", Biophysical Journal, vol. 69, pp 1528–1535, Oct., 1995.

Friedman, Richard A. et al., "New Evidence that the Hydrophobic Effect and Dispersion Are Not Major Driving Forces for Nucleotide Base Stacking", Biophysical Journal, vol. 71, pp 3523–3526, Dec., 1996.

Guo, Zhen, et al., "Direct Fluorescence Analysis of Genetic Polymorphisms by Hybridization With Oligonucleotide Arrays on Glass Supports", Nucleic Acids Research, vol. 22, No. 24, pp 5456–5465, 10/96.

Gupta, Goutam et al., "Theoretical Calculations of Base–Base Interactions in Nucleic Acids: I Stacking Interactions in Free Bases", Nucleic Acids Research, vol. 5, No. 5, May 1978, pp 1639–1673.

Jagadeeswaran et al. ,Biotechniques vol. 12, No. 3, pp 336–339.

Khrapko, K.R., et al, "A Method for DNA Sequencing by Hybridization With Oligonucleotide Matrix", DNA Sequence—J DNA Sequencing and Mapping, vol. 1, pp 375–388.

Lane, Michael, et al., "The Thermodynamic Advantage of DNA Oligonucleotide Stakcing Hybridization Reactons: Energetics of a DNA Nick", Nucleic Acid Research, 1997, vol. 25, No. 3, 12/96, pp 611–616.

Parinov, Sergei, et al., "DNA Sequencing by Hybridization to Microchip Octa– and Decanucleotides Extended by Stacked Pentanudeotides", Nucleic Acid Research, 1996, vol. 24, No. 15, pp 2998–3004, 6/96.

Planz, J.V. et al., "Development and Validation of a GBA™–Based mtDNA Sequence Evaluation System for Forensic Testing".

Paton, Adrienne W., et al., Heterogeneity of the Amino–Acid Sequences of *Escherichia coli* Shiga–Like Toxin Type–I Operons, Gene 153 (1995) 71–74.

Promega Technical Manual, printed 8/96.

Singh, Malvinder P. et al., "High–Field NMR and Restrained Molecular Modeling Studies on a DNA Heteroduplex Containing a Modified Apurinic Abasic Site in the Form of Covalently Linked 9–Aminoellipticine", Biochemistry, 1994, 33, 19271–10385.

Tautz, Diethard, "Hypervariability of Simple Sequences as a General Source for Polymorphic DNA Markers", Nucleic Acids Research, Aug. 26, 1989; 12(16):6463–71.

Ron et al., "In Situ Detection of Tandem DNA Repeat Length", Genetic analysis: Biomolecular Engineer, 13 (1996) 113–118.

Yershov, Gennady et al., "DNA Analysis and Diagnostics on Oligonucleotide Microchips", Proc. Natl. Acad. Sci. USA 93 (1996) 4913–4918.

Radtkey et al., "Rapid High Fidelity Analysis Of Simple Sequence Repeats On An Electronically Active DNA Microchip", Nucleic Acids Research, 28, 7, Apr. 2000, pp. e17–i–e17–vi.

Saenger, *Principles of Nucleic Acid Structure*, 1984, Springer–Vertag. New York, NY. XP001079083, Chapter 6: Forces Stabilizing Associations Between Bases: Hydrogen Bonding & Base Stacking.

* cited by examiner

MULTIPLEX STR DISCRIMINATION (SANDWICH)

FIG. 4A

MISMATCH - GAP (ONE REPEAT UNIT)

5' acacagactccatggtgAATGAATGAATGAATGAATGAATGAATGagggaaataagggagga 3' (SEQUENCE ID NO.5)
3' taccacTTAC    TTACTTACTTACTTACTTACTTACTTACtcccttattccctcct 5' (SEQUENCE ID NO.17)

FIG. 4B

MISMATCH - OVERLAP (ONE REPEAT UNIT)

5' acacagactccatggtgAATGAATGAATGAATGAATGAATGAATGagggaaataagggagga 3' (SEQUENCE ID NO.7)
3' tacca TTACTTACTTACTTACTTACTTACTTACTTACtcccttattccctcct 5' (SEQUENCE ID NO.17)

FIG. 4C

MATCH

5' acacagactccatggtgAATGAATGAATGAATGAATGAATGAATGagggaaataagggagga 3' (SEQUENCE ID NO.6)
3' taccacTTACTTACTTACTTACTTACTTACTTACTTACtcccttattccctcct 5' (SEQUENCE ID NO.17)

THE SANDWICH ASSAY

THE SANDWICH ASSAY
(WITH THE 2 REPEAT UNIT REPORTER)

OLIGO TABLE — TH01

| CAPTURE OLIGOS | |
|---|---|
| 3ru | 5' BIOTIN - TCCTCCCTTATTCCCTCATTCATTCATT 3' (SEQUENCE ID NO.1) |
| 4ru | 5' BIOTIN - TCCTCCCTTATTCCCTCATTCATTCATTCATT 3' (SEQUENCE ID NO.2) |
| 5ru | 5' BIOTIN - TCCTCCCTTATTCCCTCATTCATTCATTCATTCATT 3' (SEQUENCE ID NO.3) |
| 6ru | 5' BIOTIN - TCCTCCCTTATTCCCTCATTCATTCATTCATTCATTCATT 3' (SEQUENCE ID NO.4) |
| 7ru | 5' BIOTIN - TCCTCCCTTATTCCCTCATTCATTCATTCATTCATTCATTCATT 3' (SEQUENCE ID NO.5) |
| 8ru | 5' BIOTIN - TCCTCCCTTATTCCCTCATTCATTCATTCATTCATTCATTCATTCATT 3' (SEQUENCE ID NO.6) |
| 9ru | 5' BIOTIN - TCCTCCCTTATTCCCTCATTCATTCATTCATTCATTCATTCATTCATTCATT 3' (SEQUENCE ID NO.7) |
| 10ru | 5' BIOTIN - TCCTCCCTTATTCCCTCATTCATTCATTCATTCATTCATTCATTCATTCATTCATT 3' (SEQUENCE ID NO.8) |
| REPORTER OLIGOS | |
| 1 REPEAT UNITS | 5' CATTCACCAT - BODIPY TEXAS RED 3' (SEQUENCE ID NO.9) |
| 2 REPEAT UNITS | 5' CATTCATTCAC - BODIPY TEXAS RED 3' (SEQUENCE ID NO.10) |
| 0 REPEAT UNITS | 5' CACCATGGAG - BODIPY TEXAS RED 3' (SEQUENCE ID NO.11) |
| MICROVAR 9.3 | 5' CATCATTCAT - BODIPY TEXAS RED 3' (SEQUENCE ID NO.12) |
| TARGET ALLELE | |
| 5X | 5' ACACAGACTCCATGGTGAATGAATGAATGAATGAATG AGGGAAATAAGGGAGGA 3' (SEQUENCE ID NO.13) |
| 6X | 5' ACACAGACTCCATGGTGAATGAATGAATGAATGAATGAATG AGGGAAATAAGGGAGGA 3' (SEQUENCE ID NO.14) |
| 7X | 5' ACACAGACTCCATGGTGAATGAATGAATGAATGAATGAATGAATG AGGGAAATAAGGGAGGA 3' (SEQUENCE ID NO.15) |
| 8X | 5' ACACAGACTCCATGGTGAATGAATGAATGAATGAATGAATGAATGAATG AGGGAAATAAGGGAGGA 3' (SEQUENCE ID NO.16) |
| 9X | 5' ACACAGACTCCATGGTGAATGAATGAATGAATGAATGAATGAATGAATGAATG AGGGAAATAAGGGAGGA 3' (SEQUENCE ID NO.17) |
| 9.3X | 5' ACACAGACTCCATGGTGAATGAATGAATGAATGAATGATGAATGAATGAATGAATG AGGGAAATAAGGGAGGA 3' (SEQUENCE ID NO.18) |
| 10X | 5' ACACAGACTCCATGGTGAATGAATGAATGAATGAATGAATGAATGAATGAATGAATG AGGGAAATAAGGGAGGA 3' (SEQUENCE ID NO.19) |
| 11X | 5' ACACAGACTCCATGGTGAATGAATGAATGAATGAATGAATGAATGAATGAATGAATGAATG AGGGAAATAAGGGAGGA 3' (SEQUENCE ID NO.20) |

FIG. 13

OLIGO TABLE – TPOX

| CAPTURE OLIGOS | |
|---|---|
| 5ru | 5' BIOTIN – TTAGGAACCCTCACTGAATGAATGAATGAATGAATG 3' (SEQUENCE ID NO.21) |
| 6ru–12ru | SAME AS ABOVE BUT WITH APPROPRIATE NUMBER OF REPEAT UNITS |
| REPORTER OLIGOS | |
| 1 REPEAT UNIT | 5' AATGTTTGGG – BODIPY TEXAS RED 3' (SEQUENCE ID NO.22) |
| 2 REPEAT UNITS | 5' AATGAATGTTT – BODIPY TEXAS RED 3' (SEQUENCE ID NO.23) |
| 0 REPEAT UNITS | 5' TTTGGGCAAA – BODIPY TEXAS RED 3' (SEQUENCE ID NO.24) |
| TARGET ALLELE | |
| 6X | 5' TTTGCCCAAACATTCATTCATTCATTCATTCAGTGAGGGTTCCCTAAGT 3' (SEQUENCE ID NO.25) |
| 7X–13X | SAME AS ABOVE BUT WITH APPROPRIATE NUMBER OF REPEAT UNITS |

FIG. 17

OLIGO TABLE – CSF1PO

| CAPTURE OLIGOS | |
|---|---|
| 5ru | 5' GCCTTCATAGAAGATAGATTAGATAGATAGATAGATAGATAGAT 3' (SEQUENCE ID NO.26) |
| 6ru–14ru | SAME AS ABOVE BUT WITH APPROPRIATE NUMBER OF REPEAT UNITS |
| REPORTER OLIGOS | |
| 1 REPEAT UNIT | 5' AGATAGGAAG 3' (SEQUENCE ID NO.27) |
| TARGET ALLELE | |
| 6X | 5' TGTTCTAAGTACTTCCTATCTATCTATCTATCTATCTAATCTATCTATCTTCTATCTATGAAGGC 3' (SEQUENCE ID NO.28) |
| 7X–15X | SAME AS ABOVE BUT WITH APPROPRIATE NUMBER OF REPEAT UNITS |

FIG. 19

TABLE 3 – DISCRIMINATING MATCH FROM MISMATCH/GAP AND MISMATCH/OVERLAP (ONE REPEAT UNIT REPORTER)

| | TARGET GENOTYPE | | | | | | | |
|---|---|---|---|---|---|---|---|---|
| CAPTURE TYPE | 11+11 | 10+11 | 9+11 | 8+11 | 7+11 | 6+11 | 5+11 | |
| 5 | a | a | a | a | a | e | d | |
| 7 | a | a | a | e | d | d | d | |
| 9 | a | e | d | d | d | d | d | |
| HYBRID TYPE | | | | | | | | |
| GENOTYPE CODE | aaa | aae | aad | aed | add | edd | ddd | |

| | TARGET GENOTYPE | | | | | | |
|---|---|---|---|---|---|---|---|
| CAPTURE TYPE | 10+10 | 9+10 | 8+10 | 7+10 | 6+10 | 5+10 | |
| 5 | a | a | a | a | e | d | |
| 7 | a | a | e | d | d | d | |
| 9 | c | f | f | f | f | f | |
| HYBRID TYPE | | | | | | | |
| GENOTYPE CODE | aac | aaf | aef | adf | edf | ddf | |

| CODE | |
|---|---|
| GAP | a |
| OVERLAP | b |
| MATCH | c |
| GAP + OVERLAP | d |
| GAP + MATCH | e |
| OVERLAP + MATCH | f |

PROBABILITY OF 3 PADS HAVING THE SAME LETTERS (OUT OF A POSSIBLE 6) = $6^3 = 216$

FIG. 23A

TABLE 3 – DISCRIMINATING MATCH FROM MISMATCH/GAP AND MISMATCH/OVERLAP (ONE REPEAT UNIT REPORTER)

| | TARGET GENOTYPE | | | | | |
|---|---|---|---|---|---|---|
| | 9+9 | 8+9 | 7+9 | 6+9 | 5+9 | |
| CAPTURE TYPE | HYBRID TYPE | | | | | |
| 5 | a | a | a | e | d | |
| 7 | a | e | d | d | d | |
| 9 | b | b | b | b | b | |
| GENOTYPE CODE | aab | aeb | adb | edb | ddb | |

| | TARGET GENOTYPE | | | | |
|---|---|---|---|---|---|
| | 8+8 | 7+8 | 6+8 | 5+8 | |
| CAPTURE TYPE | HYBRID TYPE | | | | |
| 5 | a | a | e | d | |
| 7 | c | f | f | e | |
| 9 | b | b | b | b | |
| GENOTYPE CODE | acb | afb | efb | deb | |

| | TARGET GENOTYPE | | | | | |
|---|---|---|---|---|---|---|
| | 7+7 | 6+7 | 5+7 | 6+6 | 5+6 | 5+5 |
| CAPTURE TYPE | HYBRID TYPE | | | | | |
| 5 | a | e | d | c | f | b |
| 7 | b | b | b | b | b | b |
| 9 | b | b | b | b | b | b |
| GENOTYPE CODE | abb | ebb | dbb | cbb | fbb | bbb |

FIG. 23B

| CODE | |
|---|---|
| GAP | a |
| OVERLAP | b |
| MATCH | c |
| GAP + OVERLAP | d |
| GAP + MATCH | e |
| OVERLAP + MATCH | f |

PROBABILITY OF 3 PADS HAVING THE SAME LETTERS
(OUT OF A POSSIBLE 6) = $6^3 = 216$

HYBRIDIZATION COMPLEX FOR THE MICROVARIANT MATCH-TH01 9.3 acacagactccatggtgAATGAATGAATGAATGAATGAATGAATGAGgggaaataagggagga 3' (SEQUENCE ID NO.1)
                 TACTTACTTACTTACTTACTTACTtccctttattccctcct 5' (SEQUENCE ID NO.18)
                                          (SEQUENCE ID NO.12)

FIG. 25

SEQUENCE LISTING

```
<160> NUMBER OF SEQ ID NOS: 28

<210> SEQ ID NO 1
<211> LENGTH: 29
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 1 tcctcccttta tttccctcat tcattcatt                                    29

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 2 tcctcccttta tttccctcat tcattcattc att                               33

<210> SEQ ID NO 3
```

```
<211> LENGTH: 37
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 3 tcctcccctta tttccctcat tcattcattc attcatt                              37

<210> SEQ ID NO 4
<211> LENGTH: 41
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 4 tcctcccctta tttccctcat tcattcattc attcattcat t                         41

<210> SEQ ID NO 5
<211> LENGTH: 45
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 5 tcctcccctta tttccctcat tcattcattc attcattcat tcatt                     45

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 6 tcctcccctta tttccctcat tcattcattc attcattcat tcattcatt                 49

<210> SEQ ID NO 7
<211> LENGTH: 53
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 7 tcctcccctta tttccctcat tcattcattc attcattcat tcattcattc att            53

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 8 tcctcccctta tttccctcat tcattcattc attcattcat tcattcattc attcatt        57

<210> SEQ ID NO 9
<211> LENGTH: 10
```

```
<212> TYPE: DNA
<213> ORGANISM: Artificial Sequence
<220> FEATURE:
<223> OTHER INFORMATION: Description of Artificial Sequence: Human/
      Bodipy Texas Red

<400> SEQUENCE: 9
cattcaccat                                                              10

<210> SEQ ID NO 10
<211> LENGTH: 11
<212> TYPE: DNA
<213> ORGANISM: Artificial Sequence
<220> FEATURE:
<223> OTHER INFORMATION: Description of Artificial Sequence: Human/
      Bodipy Texas Red

<400> SEQUENCE: 10
cattcattca c                                                            11

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Human/
      Bodipy Texas Red

<400> SEQUENCE: 11
caccatggag                                                              10

<210> SEQ ID NO 12
<211> LENGTH: 10
<212> TYPE: DNA
<213> ORGANISM: Artificial Sequence
<220> FEATURE:
<223> OTHER INFORMATION: Description of Artificial Sequence: Human/
      Bodipy Texas Red

<400> SEQUENCE: 12
catcattcat                                                              10

<210> SEQ ID NO 13
<211> LENGTH: 54
<212> TYPE: DNA
<213> ORGANISM: Homo sapiens

<400> SEQUENCE: 13
acacagactc catggtgaat gaatgaatga atgaatgagg gaaataaggg agga            54

<210> SEQ ID NO 14
<211> LENGTH: 58
<212> TYPE: DNA
<213> ORGANISM: Homo sapiens

<400> SEQUENCE: 14
acacagactc catggtgaat gaatgaatga atgaatgaat gagggaaata agggagga        58

<210> SEQ ID NO 15
<211> LENGTH: 62
<212> TYPE: DNA
<213> ORGANISM: Homo sapiens

<400> SEQUENCE: 15
acacagactc catggtgaat gaatgaatga atgaatgaat gaatgaggga aataagggag      60
```

```
<210> SEQ ID NO 16
<211> LENGTH: 66
<212> TYPE: DNA
<213> ORGANISM: Homo sapiens

<400> SEQUENCE: 16
acacagactc catggtgaat gaatgaatga atgaatgaat gaatgaatga gggaaataag      60
ggagga                                                                 66

<210> SEQ ID NO 17
<211> LENGTH: 70
<212> TYPE: DNA
<213> ORGANISM: Homo sapiens

<400> SEQUENCE: 17
acacagactc catggtgaat gaatgaatga atgaatgaat gaatgaatga atgagggaaa      60
taagggagga                                                             70

<210> SEQ ID NO 18
<211> LENGTH: 73
<212> TYPE: DNA
<213> ORGANISM: Homo sapiens

<400> SEQUENCE: 18
acacagactc catggtgaat gaatgaatga atgaatgaat gatgaatgaa tgaatgaggg      60
aaataaggga gga                                                         73

<210> SEQ ID NO 19
<211> LENGTH: 74
<212> TYPE: DNA
<213> ORGANISM: Homo sapiens

<400> SEQUENCE: 19
acacagactc catggtgaat gaatgaatga atgaatgaat gaatgaatga atgaatgagg      60
gaaataaggg agga                                                        74

<210> SEQ ID NO 20
<211> LENGTH: 78
<212> TYPE: DNA
<213> ORGANISM: Homo sapiens

<400> SEQUENCE: 20
acacagactc catggtgaat gaatgaatga atgaatgaat gaatgaatga atgaatgaat      60
gagggaaata agggagga                                                    78

<210> SEQ ID NO 21
<211> LENGTH: 41
<212> TYPE: DNA
<213> ORGANISM: Artificial Sequence
<220> FEATURE:
<223> OTHER INFORMATION: Description of Artificial Sequence: Human/
      Biotin

<400> SEQUENCE: 21
ttagggaacc ctcactgaat gaatgaatga atgaatgaat g                          41

<210> SEQ ID NO 22
<211> LENGTH: 10
<212> TYPE: DNA
```

```
<213> ORGANISM: Artificial Sequence
<220> FEATURE:
<223> OTHER INFORMATION: Description of Artificial Sequence: Human/
      Bodipy Texas Red

<400> SEQUENCE: 22
aatgtttggg                                                            10

<210> SEQ ID NO 23
<211> LENGTH: 11
<212> TYPE: DNA
<213> ORGANISM: Artificial Sequence
<220> FEATURE:
<223> OTHER INFORMATION: Description of Artificial Sequence: Human/
      Bodipy Texas Red

<400> SEQUENCE: 23
aatgaatgtt t                                                          11

<210> SEQ ID NO 24
<211> LENGTH: 10
<212> TYPE: DNA
<213> ORGANISM: Artificial Sequence
<220> FEATURE:
<223> OTHER INFORMATION: Description of Artificial Sequence: Human/
      Bodipy Texas Red

<400> SEQUENCE: 24
tttgggcaaa                                                            10

<210> SEQ ID NO 25
<211> LENGTH: 53
<212> TYPE: DNA
<213> ORGANISM: Homo sapiens

<400> SEQUENCE: 25
tttgcccaaa cattcattca ttcattcatt cattcagtga gggttcccta agt            53

<210> SEQ ID NO 26
<211> LENGTH: 48
<212> TYPE: DNA
<213> ORGANISM: Homo sapiens

<400> SEQUENCE: 26
gccttcatag atagaagata gatagattag atagatagat agatagat                  48

<210> SEQ ID NO 27
<211> LENGTH: 10
<212> TYPE: DNA
<213> ORGANISM: Homo sapiens

<400> SEQUENCE: 27
agataggaag                                                            10

<210> SEQ ID NO 28
<211> LENGTH: 69
<212> TYPE: DNA
<213> ORGANISM: Homo sapiens

<400> SEQUENCE: 28
tgttctaagt acttcctatc tatctatcta tctatctatc taatctatct atcttctatc     60
tatgaaggc                                                             69
```

METHODS AND APPARATUS FOR DETECTING VARIANTS UTILIZING BASE STACKING

RELATED APPLICATION INFORMATION

This application is a continuation of U.S. Ser. No. 09/645,757, filed Aug. 24, 2000, entitled "METHODS AND APPARATUS FOR DETERMINATION OF LENGTH POLYMORPHISMS IN DNA", now issued as U.S. Pat. No. 6,395,493, which is a continuation of U.S. Ser. No. 09/030,156, filed Feb. 25, 1998, entitled "METHODS AND APPARATUS FOR DETERMINATION OF LENGTH POLYMORPHISMS IN DNA", now issued as U.S. Pat. No. 6,207,373.

Further, this application is related to Application Ser. No. 08/986,065, filed Dec. 5, 1997, entitled "METHODS AND PARAMETERS FOR ELECTRONIC BIOLOGICAL DEVICES", now issued as U.S. Pat. No. 6,051,380, which is a continuation-in-part of application Ser. No. 08/534,454, filed Sep. 27, 1995, entitled "APPARATUS AND METHODS FOR ACTIVE PROGRAMMABLE MATRIX DEVICES", now issued as U.S. Pat. No. 5,849,486, which is a continuation-in-part of application Ser. No. 08/304,657, filed Sep. 9, 1994, entitled "AUTOMATED MOLECULAR BIOLOGICAL DIAGNOSTIC SYSTEM," now issued as U.S. Pat. No. 5,632,957, which is a continuation-in-part of application Ser. No. 08/271,882, filed Jul. 7, 1994, entitled "METHODS FOR ELECTRONIC STRINGENCY CONTROL FOR MOLECULAR BIOLOGICAL ANALYSIS AND DIAGNOSTICS," now aissued as U.S. Pat. No. 6,017,696, which is a continuation-in-part of Ser. No. 08/146,504, filed Nov. 1, 1993, entitled "ACTIVE PROGRAMMABLE ELECTRONIC DEVICES FOR MOLECULAR BIOLOGICAL ANALYSIS AND DIAGNOSTICS", now issued as U.S. Pat. No. 5,605,662, all incorporated herein by reference as if fully set forth herein.

FIELD OF THE INVENTION

The methods and apparatus of these inventions relate to systems for genetic identification for disease state identification. More particularly, the methods and apparatus relate to systems for the detection of repeat unit states, such as the number of short tandem repeat units for the identification of individuals such as in a forensic or paternity sense, or for determination of disease states, such as for clonal tumor detection.

BACKGROUND OF THE INVENTION

Molecular biology comprises a wide variety of techniques for the analysis of nucleic acid and protein. Many of these techniques and procedures form the basis of clinical diagnostic assays and tests. These techniques include nucleic acid hybridization analysis, restriction enzyme analysis, genetic sequence analysis, and the separation and purification of nucleic acids and proteins (See, e.g., J. Sambrook, E. F. Fritsch, and T. Maniatis, *Molecular Cloning: A Laboratory Manual*, 2 Ed., Cold spring Harbor Laboratory Press, Cold Spring Harbor, N.Y., 1989).

Most of these techniques involve carrying out numerous operations (e.g., pipetting, centrifugation, electrophoresis) on a large number of samples. They are often complex and time consuming, and generally require a high degree of accuracy. Many a technique is limited in its application by a lack of sensitivity, specificity, or reproducibility. For example, these problems have limited many diagnostic applications of nucleic acid hybridization analysis.

The complete process for carrying out a DNA hybridization analysis for a genetic or infectious disease is very involved. Broadly speaking, the complete process may be divided into a number of steps and substeps. In the case of genetic disease diagnosis, the first step involves obtaining the sample (blood or tissue). Depending on the type of sample, various pre-treatments would be carried out. The second step involves disrupting or lysing the cells, which then release the crude DNA material along with other cellular constituents. Generally, several sub-steps are necessary to remove cell debris and to purify further the crude DNA. At this point several options exist for further processing and analysis. One option involves denaturing the purified sample DNA and carrying out a direct hybridization analysis in one of many formats (dot blot, microbead, microplate, etc.). A second option, called Southern blot hybridization, involves cleaving the DNA with restriction enzymes, separating the DNA fragments on an electrophoretic gel, blotting to a membrane filter, and then hybridizing the blot with specific DNA probe sequences. This procedure effectively reduces the complexity of the genomic DNA sample, and thereby helps to improve the hybridization specificity and sensitivity. Unfortunately, this procedure is long and arduous. A third option is to carry out an amplification procedure such as polymerase chain reaction (PCR), strand displacement amplification or other method. These procedures amplify (increase) the number of target DNA sequences relative to non-target sequences. Amplification of target DNA helps to overcome problems related to complexity and sensitivity in genomic DNA analysis. After these sample preparation and DNA processing steps, the actual hybridization reaction is performed. Finally, detection and data analysis convert the hybridization event into an analytical result.

Nucleic acid hybridization analysis generally involves the detection of a very small number of specific target nucleic acids (DNA or RNA) with an excess of probe DNA, among a relatively large amount of complex non-target nucleic acids. The substeps of DNA complexity reduction in sample preparation have been utilized to help detect low copy numbers (i.e. 10,000 to 100,000) of nucleic acid targets. DNA complexity is overcome to some degree by amplification of target nucleic acid sequences using polymerase chain reaction (PCR) and other methods. (See, M. A. Innis et al, *PCR Protocols: A Guide to Methods and Applications*, Academic Press, 1990, Spargo et al., 1996, Molecular & Cellular Probes, in regard to SDA amplification). Amplification results in an enormous number of target nucleic acid sequences that improves the subsequent direct probe hybridization step.

The actual hybridization reaction represents one of the most important and central steps in the whole process. The hybridization step involves placing the prepared DNA sample in contact with a specific reporter probe, at a set of optimal conditions for hybridization to occur to the target DNA sequence. Hybridization may be performed in any one of a number of formats. For example, multiple sample nucleic acid hybridization analysis has been conducted on a variety of filter and solid support formats (See G. A. Beltz et al., in *Methods in Enzymology*, Vol. 100, Part B, R. Wu, L. Grossman, K. Moldave, Eds., Academic Press, New York, Chapter 19, pp. 266–308, 1985). One format, the so-called "dot blot" hybridization, involves the non-covalent attachment of target DNAs to filter, which are subsequently hybridized with a radioisotope labeled probe(s). "Dot blot" hybridization gained wide-spread use, and many versions were developed (see M. L. M. Anderson and B. D. Young, in *Nucleic Acid Hybridization—A Practical Approach*, B. D. Hames and S. J. Higgins, Eds., IRL Press, Washington, D.C. Chapter 4, pp. 73–111, 1985). It has been developed for multiple analysis of genomic mutations (D. Nanibhushan and D. Rabin, in EPA 0228075, Jul. 8, 1987) and for the detection of overlapping clones and the construction of genomic maps (G. A. Evans, in U.S. Pat. No. 5,219,726, Jun. 15, 1993).

New techniques are being developed for carrying out multiple sample nucleic acid hybridization analysis on micro-formatted multiplex or matrix devices (e.g., DNA chips) (see M. Baringa, 253 Science, pp. 1489, 1991; W. Bains, 10 Bio/Technology, pp. 757–758, 1992). These methods usually attach specific DNA sequences to very small specific areas of a solid support, such as micro-wells of a DNA chip. These hybridization formats are micro-scale versions of the conventional "dot blot" and "sandwich" hybridization systems.

The micro-formatted hybridization can be used to carry out "sequencing by hybridization"(SBH) (see M. Baringa, 253 Science, pp. 1489, 1991; W. Bains, 10 Bio/Technology, pp. 757–758, 1992). SBH makes use of all possible n-nucleotide oligomers (n-mers) to identify n-mers in an unknown DNA sample, which are subsequently aligned by algorithm analysis to produce the DNA sequence (R. Drmanac and R. Crkvenjakov, Yugoslav Patent Application #570/87, 1987; R. Drmanac et al., 4 Genomics, 114, 1989; Strezoska et al., 88 Proc. Natl. Acad. Sci. USA 10089, 1992; and R. Drmanac and R. B. Crkvenjakov, U.S. Pat. No. 5,202,231, Apr. 13, 1993).

There are two formats for carrying out SBH. The first format involves creating an array of all possible n-mers on a support, which is then hybridized with the target sequence. The second format involves attaching the target sequence to a support, which is sequentially probed with all possible n-mers. Both formats have the fundamental problems of direct probe hybridizations and additional difficulties related to multiplex hybridizations.

Southern, United Kingdom Patent Application GB 8810400, 1988; E. M. Southern et al., 13 Genomics 1008, 1992, proposed using the first format to analyze or sequence DNA. Southern identified a known single point mutation using PCR amplified genomic DNA. Southern also described a method for synthesizing an array of oligonucleotides on a solid support for SBH. However, Southern did not address how to achieve optimal stringency condition for each oligonucleotide on an array.

Concurrently, Drmanac et al., 260 Science 1649–1652, 1993, used the second format to sequence several short (116 bp) DNA sequences. Target DNAs were attached to membrane supports ("dot blot" format). Each filter was sequentially hybridized with 272 labeled 10-mer and 11-mer oligonucleotides. A wide range of stringency condition was used to achieve specific hybridization for each n-mer probe; washing times varied from 5 minutes to overnight, and temperatures from 0% C to 16% C. Most probes required 3 hours of washing at 16% C. The filters had to be exposed for 2 to 18 hours in order to detect hybridization signals. The overall false positive hybridization rate was 5% in spite of the simple target sequences, the reduced set of oligomer probes, and the use of the most stringent conditions available.

A variety of methods exist for detection and analysis of the hybridization events. Depending on the reporter group (fluorophore, enzyme, radioisotope, etc.) used to label the DNA probe, detection and analysis are carried out fluorimetrically, colorimetrically, or by autoradiography. By observing and measuring emitted radiation, such as fluorescent radiation or particle emission, information may be obtained about the hybridization events. Even when detection methods have very high intrinsic sensitivity, detection of hybridization events is difficult because of the background presence of non-specifically bound materials. A number of other factors also reduce the sensitivity and selectivity of DNA hybridization assays.

One form of genetic analysis consists of determining the nature of relatively short repeating sequences within a gene sequence. Short tandem repeats (STR's) have been identified as a useful tool in both forensics and in other areas (paternity testing, tumor detection, D. Sidransky, genetic disease, animal breeding). Indeed, the United States Federal Bureau of Investigation has announced that it is considering the use of short tandem repeat sequences for forensic purposes. (Dr. Bruce Budowle, DNA Forensics, Science, Evidence and Future Prospects, McLean, Va. November, 1997).

Various proposals have been made for identifying, amplifying, detecting and using polymorphic repeat sequences. For example, Tautz PCT W090/04040-PCT/EP98/01203, in an application entitled "Process for the Analysis of Length Polymorphorisms in DNA Regions" (translated from German), discloses a process for the analysis of length polymorphisms in regions of simple or cryptically simple DNA sequences. Tautz discloses a method which includes these steps of addition of at least one primer pair onto the DNA that is to be analyzed, wherein one of the molecules of the primer pair is substantially complementary to the complementary strands of the 5' respectively 3' flank of a simple or cryptically simple DNA sequence and wherein the addition takes place within orientation that is such that the synthesis products obtained from a primer controlled polymerization reaction with one of the two primers can be used, following denaturation, as matrices for the addition of the other primer, performing a primer-controlled polymerization reaction and separating, such as by normal gel electrophoresis the products and analyzing the polymerase chain reaction products.

Caskey et al. at the Baylor College of Medicine also detected polymorphisms in a short tandem repeat by performing DNA profiling assays. In Caskey et al., U.S. Pat. No. 5,364,759, issued Nov. 15, 1994, entitled "DNA Typing With Short Tandem Repeat Polymorphisms and Identification of Polymorphic Short Tandem Repeats" discloses a method including steps of extracting DNA from a sample to be tested, amplifying the extracted DNA and identifying the amplified extension products for each different sequence. Caskey required that each different sequence be differentially labeled. A physical separation was performed utilizing electrophoresis.

C. R. Cantor and others more recently disclosed a technique for scoring short tandem DNA repeats. The method is disclosed in Yarr, R. et al., "In Situ Detection of Tandem DNA Repeat Length", Genetic Analysis: Biomolecular Engineering, 13(1996) 113–118, and PCT Application W096/3673 1, PCT/US96/06527 entitled "nucleic Acid Detection Methods". These disclose hybridization of an oligonucleotide target containing tandem repeats embedded in a unique sequence with a set of complementary probes containing tandem repeats of known lengths. Single-stranded loop structures result in duplexes containing a mismatched (defined there to be a different) number of tandem repeats. When a matched (defined there to be identical) number of tandem repeats existed on the duplex, no loop structure formed. The loop structures were digested with a single-stranded nuclease. Differential wavelength, such as through differentially colored fluoriflors of the various length probes identified where matched sites existed. No express use of electrophoretic separation was required in accordance with this method.

Despite the knowledge of the existence of polymorphism in repeat units now for approximately 15 years, as well as their known desirability for application in forensics and genetic testing, commercially acceptable implementations have yet to be achieved.

SUMMARY OF THE INVENTION

Methods and apparatus are provided for the analysis and determination of the nature of repeat units in a genetic target. In one method of this invention, the nature of the repeat units in the genetic target is determined by the steps of providing a plurality of hybridization complex assays arrayed on a plurality of test sites, where the hybridization complex assay includes at least a nucleic acid target containing a simple repetitive DNA sequence, a capture probe having a first unique flanking sequence and n repeat units, where n=0, 1, 2 . . . , being complementary to the target sequence, and a reporter probe having a selected sequence complementary to the same target sequence strand wherein the selected sequence of the reporter includes a second unique flanking sequence and m repeat units, where m=0, 1, 2 . . . , but where the sum of repeat units in the capture probe plus reporter probe is greater than 0 (n+m>0). In accordance with this method, the sequence of the capture probe differs at least two test sites. The hybridization complex assays are then monitored to determine concordance and discordance among the hybridization complex assays at the test sites as determined at least in part by hybridization stability. Ultimately, the nature of the repeat units in the target sequence may be determined based upon the concordant/discordant determination coupled with knowledge of the probes located in the hybridization complex at that site.

By way of example, in implementation of this method, assume that a target contains six repeat units. In a system simplified merely for expository convenience, the plurality of hybridization complex assays might be three assays arrayed on an APEX type bioelectronic system, wherein a first assay includes a capture probe having four repeat units (n=4), the second assay has a capture probe with five repeat units (n=5) and the third assay has capture probes with six repeat units (n=6). If the reporter probe is selected to have one repeat unit (m=1), the total number of repeat units at the first assay will be five (n+m=4+1=5), the total number of repeat units at the second assay will equal six (n+m=5+1=6), and the total number of repeat units at the third assay will equal seven (n+m=6+1=7). The second test site will be the concordant test site since the number of repeat units in the target in this case equals the number of repeat units in the capture plus the reporter probes, that is it is the test site with six repeat units both in the target and in the combination of the capture probe and the reporter probe. Utilizing the knowledge regarding probe placement, the second test site is known to include a capture probe having five repeat units (n=5), such that when coupled with the knowledge of the reporter probe including one repeat unit, the total number of six repeat units in the target is determined.

In the preferred embodiment of these inventions, electronically aided hybridization or concordance and discordance determination, or both, are utilized in the process. In one aspect, during the hybridization of the nucleic acid target with the capture probe and/or the reporter probe, electronic stringent conditions may be utilized, preferably along with other stringency affecting conditions, to aid in the hybridization. This technique is particularly advantageous to reduce or eliminate slippage hybridization among repeat units, and to promote more effective hybridization. In yet another aspect, electronic stringency conditions may be varied during the hybridization complex stability determination so as to more accurately or quickly determine the state of concordance or discordance.

In yet another aspect of this invention, a method is provided for the determination of the nature of the repeat units in a genetic target by providing a bioelectronic device including a set of probes arrayed at a set of test sites, the probes having a first unique flanking sequence, a second unique flanking sequence, and an intervening repeat unit series having variable numbers of repeat units. The target is hybridized with the set of probes at the set of test sites, under electronic stringency hybridization conditions, and the concordance/discordance at the test sites is then determined. In the preferred embodiment, the concordance/discordance is determined at least in part through the use of electronic hybridization stability determinations. The concordant test site indicates which probe includes the number of repeat units identical to that in the target. In a variation of this embodiment, electronic stringency control is utilized only during the concordance/discordance determination.

In yet another aspect of this invention, methods and apparatus are provided for the determination of target alleles which vary in size in a sample. A platform is provided for the identification of target alleles which includes probes selected from the group consisting of (i) a probe having a first unique flanking sequence, an intervening repeat region and a second unique flanking sequence, and (ii) a sandwich assay comprising a capture probe having a first unique flanking sequence and 0,1,2 . . . repeat units and a reporter probe having 0,1,2 . . . repeat units in sequence with a second unique flanking sequence. Thereafter, the target is hybridized with the probes, preferably under electronic stringent conditions so as to aid in proper indexing, or alternatively, utilizing electronic stringency conditions during subsequent steps, or using electronic stringency both during hybridization and at later steps, thereafter determining concordance and discordance at the test sites as determined at least in part by hybridization stability.

In one aspect of the inventions, the location of the concordant test site represents the nature of the target sequence repeat units by the number of repeat units present in the target, and that in turn is based upon the knowledge of the probes located at that test site. Namely, the particular probes associated with a given physical test site typically will be known in terms of their sequence, especially including the number of repeat units, and the physical position of those test sites results in a knowledge for the concordant sites of the nature of the target, especially the number of repeat units. Typically, at a concordant test site, the number of repeat units in the target equals the sum of the number of repeat units in the capture probe and the number of repeat units in the reporter probe.

One advantageous aspect of the inventions is that the methods and apparatus are effective in determining the presence of microvariants in the target sequence. Such microvariants may include one or more deletions, insertions, transitions and/or transversions. These may be for a single base or for more than a single base. Deletions or insertions within repeat units can be detected by gel separation methods when using highly controlled conditions. This requires single base resolution and is near the limit of detection for most gel separation techniques. For transitional or transversional mutations, the size of the allele doesn't change, even though the sequence has become altered. Conventional gel sieving methods have a very difficult time detecting these types of mutations, and recent findings by other investigators (Sean Walsh, Dennis Roeder, DNA Forensics: Science, Evidence and Future Prospects, McLean, Va. November, 1997) suggest that transitional and transversional mutations can cause subtle anomalies resulting in difficult gel analysis sometimes resulting in obfuscation of STR analysis. Our method is an hybridization technique and is quite adept at reliably detecting single nucleotide polymorphisms as described above. Additionally, by designing specific capture and reporter oligonucleotides these assays can be done on the same platform used to discriminate the nature of STR alleles by repeat unit number. The general strategy of designing capture oligos for microvariant analysis is the same as it is for integral repeat units, however reporter oligos may differ in that they may or may not contain unique flanking sequence. The condition of effectively determining concordance by maximizing the hybridization complex stability remains since oligo design parameters which yield base stacking (as described above) are still followed.

In yet another aspect of these inventions, various additional steps may be utilized in order to promote distinguishing concordant and discordant test sites. One mode of concordance may be that in which there is a complementary match of bases in the hybridization complex including the capture, reporter and target in the sandwich assay format. In yet another highly advantageous arrangement, the use of juxtaposed terminal nucleotides of the reporter and capture may be utilized, wherein their contiguous nature permits interaction, such as base stacking. Advantageously, the juxtaposed terminal nucleotide identities may be selected, as allowed by the existing repeat unit or otherwise relevant sequence, so as to increase the energy difference between concordance and discordance. It has been reported that base stacking between different bases varies in stability through an approximately 4-fold range (Saenger, Principles of Nucleic Acid Structure, 1984, Springer-Verlag, New York, N.Y.). Experimental results have shown at least a ten-fold, and often times at least more than twenty-fold, improvement in discrimination ratios for the pairings 5'G-A3' versus 5'T-A3', when analyzed in our system. While this result is generally in concert with the published findings that 5'G-A3' base stacking provides greater stability than 5'T-A3' pairs, the differential stability increase seen with our assay greatly exceeds the reported values. It is highly beneficial that this invention exploits this natural condition to provide a superior assay advantage. In yet other embodiments, the terminal nucleotides may be modified to increase base stacking effects, such as with the addition of propynyl groups, methyl groups or cholesterol groups. In yet another related aspect, ligation techniques may be utilized, such as enzyme ligation or chemical ligation, so as to increase the energy difference between a concordant and discordant site.

Discordance may be manifested in various ways, such as in the sandwich assay format wherein a gap or overlap exists, or in the loop out method where a loop out exists. Further, discordance may exist in the repeat region where there is a base variation, such as a deletion, insertion, transition and/or transversion.

In distinguishing concordant and discordant test sites, the distinction is preferably drawn in part based on hybridization stability. Hybridization stability may be influenced by numerous factors, including thermoregulation, chemical regulation, as well as electronic stringency control, either alone or in combination with the other listed factors. Through the use of electronic stringency conditions, in either or both of the target hybridization step or the reporter oligonucleotide stringency step, rapid completion of the process may be achieved. Electronic stringency hybridization of the target is one distinctive aspect of this method since it is amenable with double stranded DNA and results in rapid and precise hybridization of the target to the capture. This is desirable to achieve properly indexed hybridization of the target DNA to attain the maximum number of molecules at a test site with an accurate hybridization complex. By way of example, with the use of electronic stringency, the initial hybridization step may be completed in ten minutes or less, more preferably five minutes or less, and most preferably one minute or less. Overall, the analytical process may be completed in less than half an hour.

As to detection of the hybridization complex, it is preferred that the complex is labeled. Typically, in the step of determining concordance and discordance, there is a detection of the amount of labeled hybridization complex at the test site or a portion thereof. Any mode or modality of detection consistent with the purpose and functionality of the invention may be utilized, such as optical imaging, electronic imaging, use of charge coupled devices or other methods of quantification. Labeling may be of the target, capture or reporter. Various labeling may be by fluorescent labeling, colormetric labeling or chemiluminescent labeling. In yet another implementation, detection may be via energy transfer between molecules in the hybridization complex. In yet another aspect, the detection may be via fluorescence perturbation analysis. In another aspect the detection may be via conductivity differences between concordant and discordant sites.

In yet another aspect of these inventions, a redundant assay may be conveniently performed. In one implementation, a serial redundant assay may be utilized, such as where after an initial hybridization complex assay is performed, the stringency conditions are increased so as to effect denaturation, thereby removing the reporter from the first hybridization complex assay. A second reporter may then be hybridized to the remaining complex target and capture probe, wherein the second reporter includes a number of repeat units which differs from the number or type of repeat units in the first reporter. In this way, through the practice of the other steps as described for other applications, the physical test site at which concordance exists will have moved. The result is that a redundant assay has been performed on the same device and sample material.

Yet another redundant assay may be performed wherein multiple, e.g., two or more, independent sets of assays exist. A first reporter is hybridized to a first set of assays, and a second reporter is hybridized to a second set of assays, wherein the number of repeat units in the first reporter differs from the number or nature of repeat units in the second reporter. Determination of concordance/discordance at the test site of the arrays, when coupled with the knowledge of the probes located as those test sites, provides two complexes from the hybridization assays for confirmation of the target repeat number or nature.

The systems and methods of these inventions are particularly useful for determining the nature of complex samples, such as heterozygous samples, and mixed samples such as those from multiple sources or donors. In application, the methods and systems of these inventions may be utilized for a broad array of applications. Among them include identification, such as for paternity testing or for other forensic use. Yet another application is in disease diagnostics, such as for the identification of the existence of a clonal tumor, where the tumor includes repeat units of a nature or number different than the patient's undiseased genetic state.

Accordingly, it is an object of this invention to provide methods and systems for the rapid identification of the nature and/or number of repeat units in a polymorphic system.

It is yet a further object of this invention to provide methods and apparatus which may effectively provide for genetic identification.

It is yet a further object of this invention to provide systems and methods for the accurate detection of diseased states, especially clonal tumor disease states, neurological disorders and predisposition to genetic disease.

It is yet a further object of this invention to provide a rapid and effective system and methods for identification, such as in forensics and paternity applications.

BRIEF DESCRIPTION OF THE DRAWINGS

FIGS. 4A, 4B and 4C show a detailed sequence listing for a multiplex assay of the TH01 locus, evidencing a gap, an overlap and a match, respectively, corresponding to the diagrammatic representations of FIGS. 3A, 3B and 3C.

FIG. 13 is a chart showing the specific olignucleotides utilized for capture sequences, reporter sequences and the target alleles in the TH01 locus.

FIG. 17 is a table of the nucleotide sequences for the TPOX capture oligonucleotides, reporter oligonucleotides and target allele for the TPOX locus.

FIG. 19 is a table of the capture oligonucleotides, reporter oligonucleotides and target alleles in the CSF1PO alleles.

FIGS. 23A and B are tables showing the discrimination of match from mismatch/gap and mismatch/overlap for various combinations.

FIG. 25 shows a detailed sequence listing for a multiplex TH01 microvariant assay.

DETAILED DESCRIPTION OF THE INVENTION

Figure 1A:
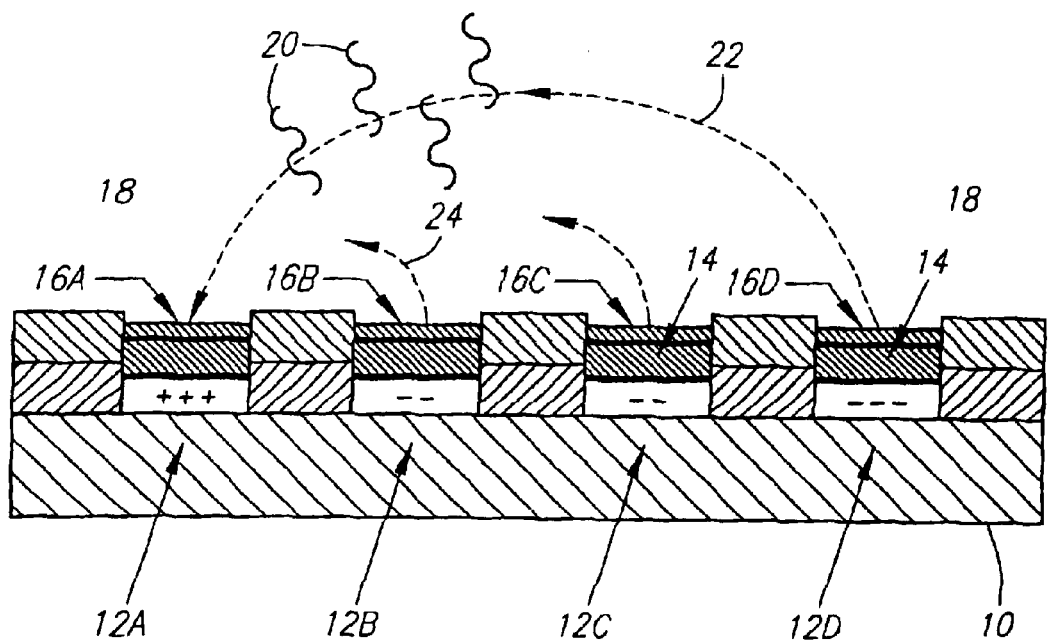
FIG. 1A is a cross sectional view of one embodiment of an active matrix device useful in accordance with the methods of this invention.
Figure 1B:
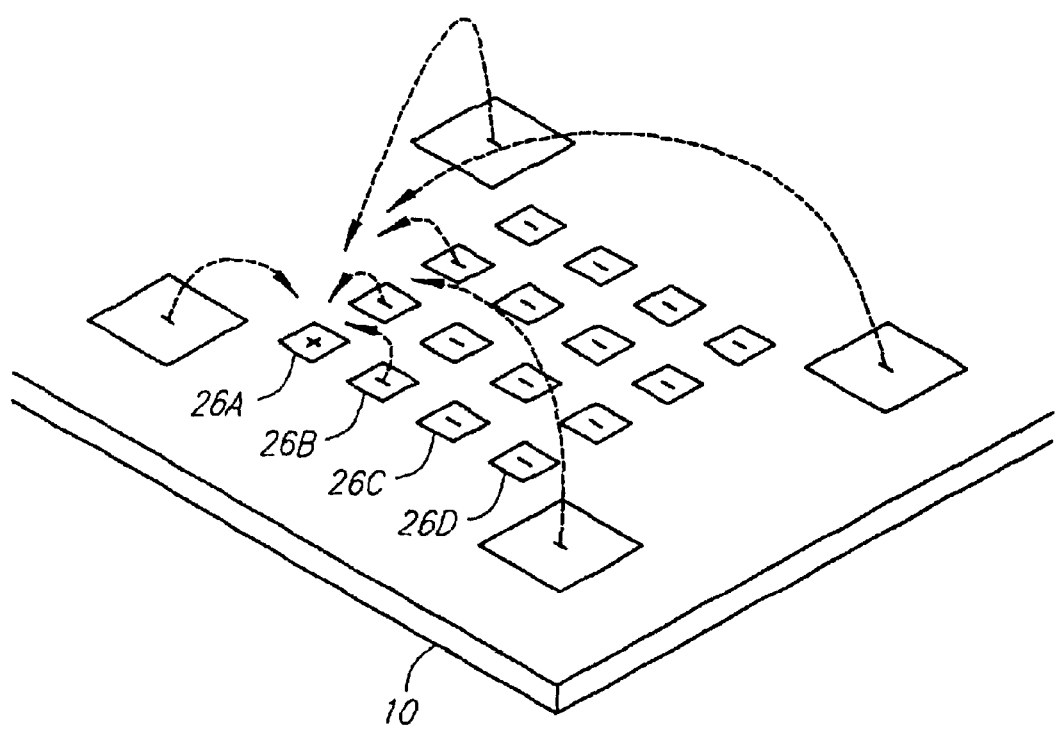
FIG. 1B is a perspective view of an active array device useful with the methods of this invention.

FIGS. 1A and 1B illustrate a simplified version of the active programmable electronic matrix hybridization system for use with this invention. Generally, a substrate 10 supports a matrix or array of electronically addressable microlocations 12. For ease of explanation, the various microlocations in FIG. 1A have been labeled 12A, 12B, 12C and 12D. A permeation layer 14 is disposed above the individual electrodes 12. The permeation layer permits transport of relatively small charged entities through it, but limits the mobility of large charged entities, such as DNA, to keep the large charged entities from easily contacting the electrodes 12 directly during the duration of the test. The permeation layer 14 reduces the electrochemical degradation which would occur in the DNA by direct contact with the electrodes 12, possibility due, in part, to extreme pH resulting from the electrolytic reaction. It further serves to minimize the strong, non-specific adsorption of DNA to electrodes. Attachment regions 16 are disposed upon the permeation layer 14 and provide for specific binding sites for target materials. The attachment regions 16 have been labeled 16A, 16B, 16C and 16D to correspond with the identification of the electrodes 12A–D, respectively.

In operation, reservoir 18 comprises that space above the attachment regions 16 that contains the desired, as well as undesired, materials for detection, analysis or use. Charged entities 20, such as charged DNA are located within the reservoir 18. In one aspect of this invention, the active, programmable, matrix system comprises a method for transporting the charged material 20 to any of the specific microlocations 12. When activated, a microlocation 12 generates the free field electrophoretic transport of any charged functionalized specific binding entity 20 towards the electrode 12. For example, if the electrode 12A were made positive and the electrode 12D negative, electrophoretic lines of force 22 would run between the electrodes 12A and 12D. The lines of electrophoretic force 22 cause transport of charged binding entities 20 that have a net negative charge toward the positive electrode 12A. Charged materials 20 having a net positive charge move under the electrophoretic force toward the negatively charged electrode 12D. When the net negatively charged binding entity 20 that has been functionalized contacts the attachment layer 16A as a result of its movement under the electrophoretic force, the functionalized specific binding entity 20 becomes covalently attached to the attachment layer 16A.

Before turning to a detailed discussion of the inventions of this patent, the general matter of terminology will be discussed. The term "short tandem repeat" (STR) as used herein refers to a locus containing simple sequence motifs which are tandemly repeated the variable number of times at different alleles of that locus. A repeat unit or repeat units typically refers to individual simple sequence motifs which are repeated in a short tandem repeat. Repeat units may be, by way of examples, complete repeat units which contain identically repeating simple sequence motifs, or may be partial repeat units, such as where there is some difference between repeat units, such as in the existence of microvariants between repeat units. A concordant test site is taken to be a test site exhibiting a relative or local maxima of hybridization complex stability. By way of example, a concordant test site may be one wherein the number of repeat units in the target is equal to the number of repeat units in a capture plus the number of repeat units in a reporter probe for a multiple system, or wherein the number of repeat units in the target equals the number of repeat units in a probe. In yet another example of a concordant test site, if partial repeat units are present, a concordant test site may be manifested by a site where the repeat units in the target are substantially similar to the nature of the repeat units in the capture plus probe, or single probe, as appropriate. A discordant site, on the other hand, is a site exhibiting a relatively lower level of hybridization complex stability relative to at least one other site. Examples of test sites which typically would be termed discordant would be those where there exists a gap, overlap, point mutation (e.g., single base variation such as deletion, insertion, transition and transversion), point mutations plus overlap, point mutations plus gap, single nucleotide variants or other microvariants.

A hybridization complex assay in a multiplex system, such as in a sandwich assay, typically will include a target, a capture and a reporter. A hybridization complex assay in a loopout application includes at least typically a target and a probe. An array as used herein typically refers to multiple test sites, minimally two or more test sites. The typical number of test sites will be one for each allele of the locus. The number of loci required for a test will vary depending on the application, with generally one for genetic disease analysis, one to five for tumor detection six, eight, nine thirteen or more for paternity testing and forensics. The physical positioning of the test sites relative to one another may be in any convenient configuration, where linear or in an arrangement of rows and columns.

Figure 2:
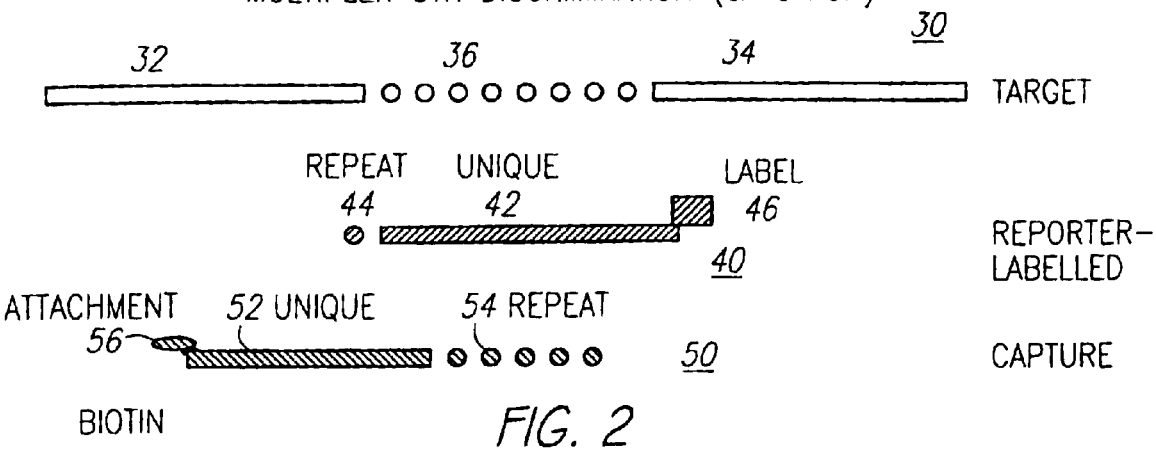
FIG. 2 is a symbolic drawing of the components of a multiplex assay, including a target, a reporter and a capture sequence.

FIG. 2 shows a symbolic drawing of the components of a multiplex assay. A target 30 includes a first unique flanking region 32, a second unique flanking region 34 and one or more repeat units 36 disposed between the first unique flanking region 32 and the second unique flanking region 34. The target 30 may be a single or double stranded nucleic acid from specific loci, such as TH01. A reporter 40 includes at least a unique sequence region 42, and optionally includes one or more repeat units 44 disposed at the terminal end of the unique sequence region 42. The reporter 40 may have no repeat units 44, or may include one or more repeat units 44. If the reporter 40 is to be labeled, a label 46 is associated therewith. Typically, the unique sequence region 42 of the reporter 40 is complementary to the second unique flanking region 34 of the target 30. The capture 50 includes a capture unique sequence region 52 and one or more repeat units 54 which are adjoined to the terminal end of the capture unique sequence region 52. If the capture 50 is to be attached to a solid support or other anchoring medium, an attachment element 56, such as biotin may be utilized.

Figure 3A:
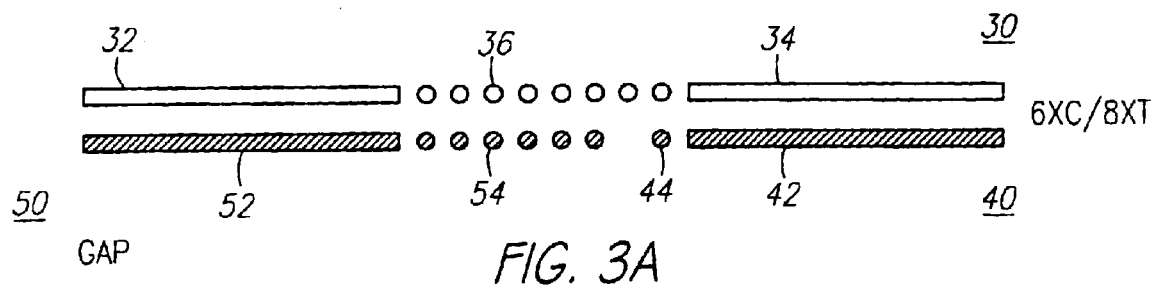
FIGS. 3A, 3B and 3C are diagrammatic sketches of the multiplex assay including a target, reporter and capture sequence in which there is existing a gap, overlap and match, respectively.
Figure 3B:
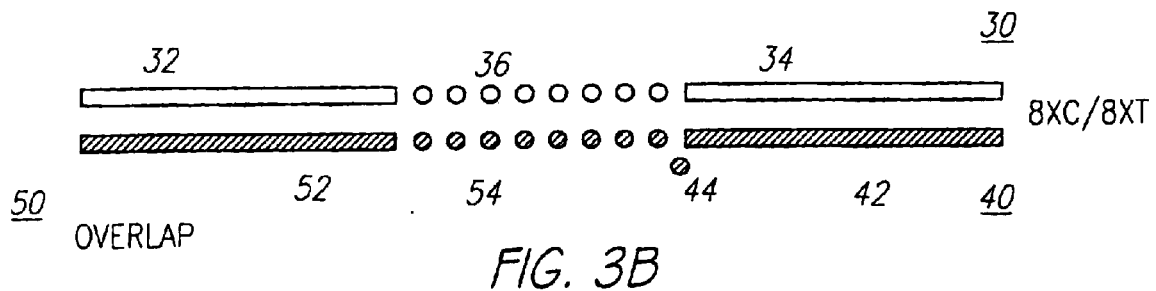
Figure 3C:
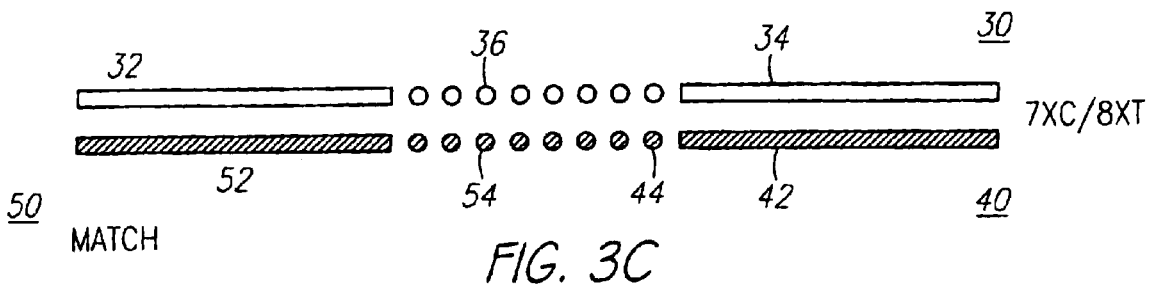

FIGS. 3A, 3B and 3C are diagrammatic sketches of the multiplex assay including a target, reporter and capture sequence in which there exists a gap, overlap and match, respectively. For simplicity, the numbering of FIG. 2 will be adopted here for corresponding structures. In FIG. 3A, a gap condition exists. Broadly, the target 30 is hybridized to the reporter 40 and to the capture 50. More particularly, the second unique flanking region 34 is hybridized to the complementary strand comprising the unique sequence region 42 of the reporter 40. Similarly, the first unique flanking region 32 of the target 30 is hybridized to the complementary capture unique sequence region 52 of the capture 50. The target 30 includes eight repeat units 36 in this example. The structure as best described applies equally to FIGS. 3A, 3B and 3C. FIG. 3A depicts a gap region 56, which results from the capture 50 having six repeat units 54 and the reporter 40 having one repeat unit 44. Thus, the total number of repeat units 44, 54 in the reporter plus capture is seven, which is one less than the total number of repeat units 36 in the target 30. In FIG. 3B, an overlap condition is shown. Here, the capture includes eight repeat units 34, and the reporter 40 still includes a single repeat unit 44. Here, the total number of repeat units 34, 44 between the capture 50 and reporter 40 is nine, exceeding the number of repeat units 36 in the target 30, whereby one repeat unit is overlapped, here shown to be the repeat unit 44 associated with the reporter 40. FIG. 3C shows a match between the target 30 and the reporter 40 plus capture 50. There are seven repeat units 34 associated with the capture 50 and one repeat unit 44 associated with the reporter 40. Accordingly, the number of repeat units 36 in the target 30 equals the sum of the repeat units 34 in the capture 50 plus the number of repeat units 44 in the reporter 40.

FIGS. 4A, 4B and 4C show one example of specific nucleotide sequences corresponding to the examples of FIGS. 3A, 3B and 3C. Note that the left to right orientation of FIGS. 3A, 3B and 3C is reversed left to right for FIGS. 4A, 4B and 4C. FIG. 4A shows a gap condition wherein the gap 56 is disposed between the repeat unit 44 of the reporter 40 and the terminal repeat unit (5' CATT3') adjacent the gap 56 of the capture 50. In FIGS. 4A, 4B and 4C, the base repeat unit 36 of the target 30 is 5'AATG3', and accordingly, its complement base sequence is 5° CATT3' 44, 54. In FIGS. 4A, 4B and 4C, the nucleotides of the base repeat unit are shown in capital letters. This is done to designate those units in distinction to the nucleotides forming the first unique flanking region 32 and second unique flanking region 34 of the target 30 as well as the unique region sequence 42 of the reporter 40 and the capture unique sequence region 52 of the capture 50. As can be seen, the nucleotides in the hybridized strands are paired, namely A-T and G-C pairs are complementary. FIG. 4B shows a mismatch with an overlap of one repeat unit. Specifically, the base repeat unit 44 comprising the series 5' CATT3' is displaced from a hybridized condition with the base unit 36 adjacent the second unique flanking region 34 of the target 30. As shown, the 5' terminal nucleotide (designated "c") of the unique sequence region 42 of the reporter 40 is shown as being slightly displaced from complete hybridization with the complementary "g" terminal nucleotide of the second unique flanking region 34 of the target 30. This depiction is optional, and may also include the condition in which the terminal nucleotide of the unique sequence region 42 is in a hybridized condition with the terminal nucleotide of the second unique flanking region 34 of the target 30. FIG. 4C shows a match condition, where in this example, the nature of the repeat region, that is both number of repeat units partial and whole, and the complementarity of the sequence match., In the matched condition of FIG. 4C, the 5' terminal nucleotide "C" of the repeat unit 44 of the reporter 40 is adjacent and contiguous with the 3' terminal nucleotide "T" of the base repeat unit 54 of the capture 50, permitting base stacking between the 5' "C" of the repeat unit 44 of the reporter 40 and the 3' "T" of the base repeat unit 54 of the capture oligonucleotide 50. The two base stacked nucleotides are underlined in FIG. 4C. In a preferred embodiment, the hybridization complex may anchored via the capture oligo 50 which would contain the appropriate attachment chemistry, preferably biotin at its 5' terminus. Also in a preferred embodiment, the hybridization complex would be labeled via the reporter oligo 40 with an appropriate molecule, preferably a chromophore at it's 3' end.

The nature of a repeat unit is defined here as comprised of both the number of whole (or integral) repeat units and partial repeat units. Partial repeat units also known as microvariants or cryptically simple sequence, may be comprised of single nucleotide divergences from the most common repeat unit sequence. These divergences may consist of insertions, deletions, transition or transversion polymorphisms of the simple repeat sequence. Since all prior methods for the analysis of STR loci have relied on size, or the number of nucleotides, information on the frequency of transition and transition repeat unit polymorphisms is scant. However other investigators have recently recognized their significance and it is likely that methods which can efficiently detect them will be valuable (Sean Walsh and Dennis Roeder, DNA Forensics, Science, Evidence and Future Prospects, McLean, Va., November 1997).

Figure 26:
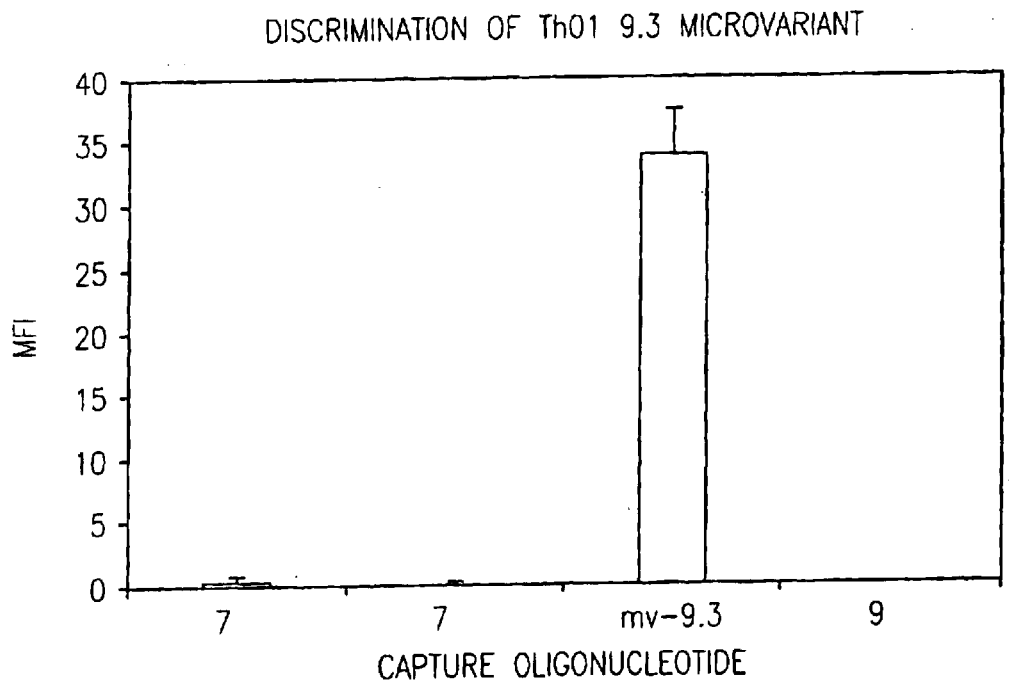
FIG. 26 is a graph of fluorescence intensity (MFI) as a function of capture oligonucleotide number or nature for the detection of the microvariant allele THO19.3.

FIG. 25 demonstrates how this invention detects the presence of a common microvariant TH01 9.3. Two new entities are presented here: a microvariant target sequence 70 containing the partial repeat unit 71 ATG and a microvariant reporter oligonucleotide 80 which is complementary to 71 and the seven 5' adjacent nucleotides. FIG. 25 shows the relationship of the DNA subsequences when the nature of the target allele is nine whole repeat units and one partial repeat, resulting in a matched concordancy. Elements which have been discussed before in FIGS. 4A–4C have retained their numerical appellation, and novel features have been labeled with new numbers. Therefore the target sequence 70 is made up of a first unique sequence 34, integral repeat sequence 36, second unique flanking sequence 32 and presents partial repeat sequence 71. The capture sequence 50 is identical to that described in FIG. 4A, with the exception that it has only three repeat units 54. The microvariant reporter 80 is similar to reporter 40 in that it has repeat sequence 44 but differs by a lack of unique flanking sequence and by the inclusion of sequence 81 which is complementary to the target 70 partial repeat unit 71. The reporter 80 stability is enhanced by two features. First it is complementary only to the microvariant region and second, it will base stack and therefore attain concordancy or a local maxima of stability only at the site which contains the 3ru capture oligo. One practiced in the art will realize how to apply this invention to microvariant sequences which differ from the TH01 9.3 sequence. FIG. 26 demonstrates the effectiveness of this method.

Selection of the adjacent or proximal nucleotides so as to increase the energy difference between concordant and discordant test sites is advantageously employed. A detailed discussion of such selections or modifications, such as in the use of terminal nucleotide base stocking, or modifications of terminal nucleotides such as with propynyl groups, methyl groups or cholesterol groups, or through the use of ligation techniques such as enzymatic ligation or chemical ligation are discussed further, below.

FIGS. 5A–5G depict a diagrammatic representation of a multiplex system. The hybridization complex used in this system is sometimes termed a sandwich assay. Again, for expository convenience, the numbering adopted corresponds to that utilized with FIG. 2, FIGS. 3A, 3B and 3C and FIGS. 4A, 4B and 4C. In each of the depictions, a target 30 has a unique flanking region 32 and a second unique flanking region 34, with an intervening set of repeat units 36. In the example, the number of repeat units 36 is 8. The reporter 40 includes a unique sequence region 42 which is complementary to the second unique flanking region 34, and includes in this example one repeat unit 44 at the terminal end of the reporter. The capture 50 includes a capture unique sequence region 52 and, in this example, multiple repeat units 54 at the terminal end of the capture 50. The capture unique sequence region 52 is complementary to the first unique flanking region 32.

Figure 5A:
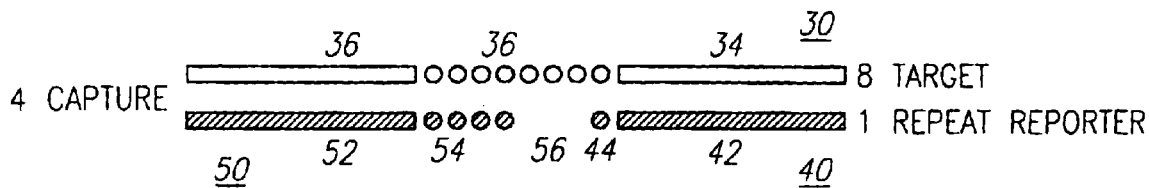
FIGS. 5A–5G depict a diagrammatic view of a sequence of multiplex assays showing a target with eight repeat units, a reporter with a single repeat unit and capture sequences including from four to ten repeat units, in FIGS. 5A–5G, respectively.

FIG. 5A shows a capture 50 with 4 repeat units 54. Since the sum of the number of repeat units 54 in the capture 50 plus the number of repeat units 44 in the reporter 40 (4+1) is less than the number of repeat units 36 in the target 30 (eight) a gap 56 exists. The gap as shown in FIG. 5A is substantially of the length of 3 repeat units 36, 44, 54. As a matter of terminology, the number of repeat units 54 in the capture 50 is sometimes denominated an "N capture", where N equals the number of base repeat units 54 in the capture 50 plus the number of base repeat units 44 in the reporter 40. With this terminology, a match exists with a N capture where N equals the number of repeat units 36 in the target 30. Thus, in the example of FIG. 5D, wherein a match condition exists, a capture 50 having 7 repeat units 54 may be also denominated an "8 capture" since the capture 50 having 7 repeat units 54 when used with these selected reporter 40 having a single repeat unit 44 provides a match in that the total number of repeat units 44, 54 equals the number of repeat units 36 in the target. It will be appreciated by those skilled in the art that various naming or number conventions may be utilized to accurately describe the underlying arrangements, and it is those underlying arrangements which comprise the inventions herein, and not the naming or numbering conventions adopted.

Figure 5B:
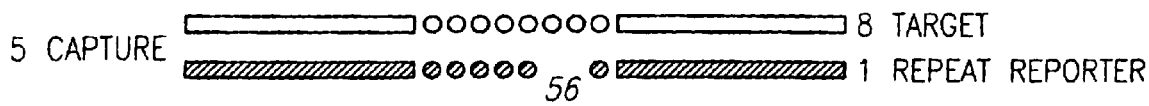
Figure 5C:
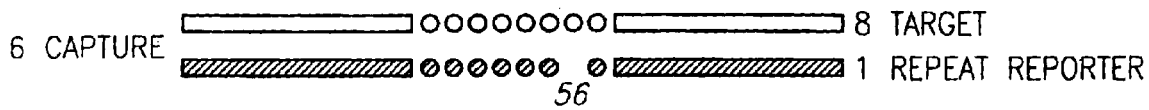
Figure 5D:

FIG. 5B shows a capture 50 having 5 repeat units 54, wherein a gap 56 of the length of substantially 2 repeat units 36, 44, 54 exists. FIG. 5C shows a capture 50 having 6 repeat units 54, wherein a gap 56 of substantially the length of a single repeat unit 36, 44, 56 exists. FIG. 5D shows a match condition with a capture 50 having 7 repeat units 54 and a reporter 40 having a single repeat unit 44 equals the number of repeat units 36 in the target 30.

Figure 5E:
Figure 5F:
Figure 5G:
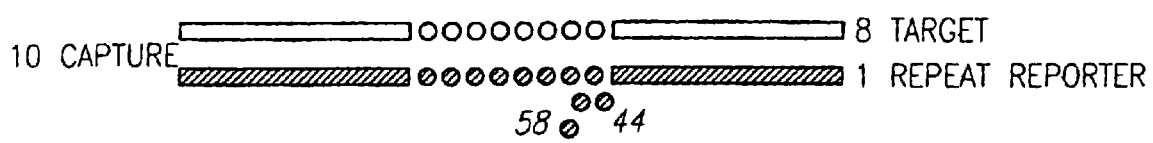

FIGS. 5E, 5F and 5G show an overlap condition. FIG. 5E shows a capture 50 with 8 repeat units 54. As depicted, the reporter 40 repeat unit 44 is shown as being in a substantially non-hybridized condition with the target 30. FIG. 5F shows a capture 50 with 9 repeat units 54, wherein a terminal repeat unit 58 of the capture 50 and the repeat unit 44 of the reporter 40 are both in a substantially non-hybridized condition with respect to the target 30. FIG. 5G shows a capture 50 having 10 repeat units 54, such that the two terminal repeat units 58 of the capture 50 and the repeat unit 44 of the reporter 40 are in a substantially non-hybridized relationship with the target 30.

Figure 6:
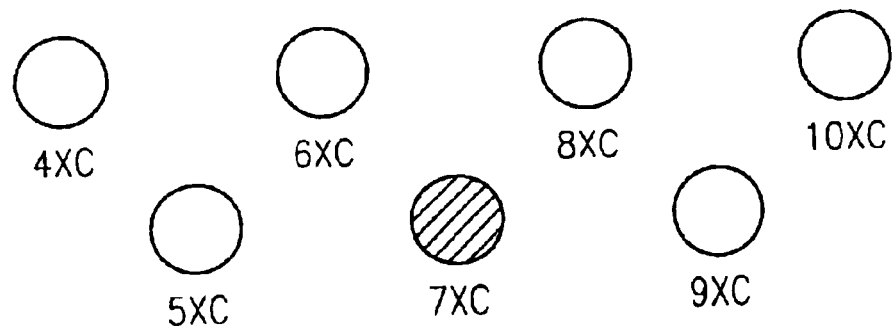
FIG. 6 shows a plan view of an array of test sites for a sandwich assay, with the concordant test site depicted as shaded to represent the presence of hybridization complex.

FIG. 6 shows a plan view of an array of test sites for use in a multiplex assay, such as a sandwich assay. The concordant test site is determined to be at the site containing the 7 repeat unit capture. This figure depicts an assay done with a 1 repeat unit reporter, therefore one can determine that the target must contain 8 repeat units since at the concordant site, the number of repeat units in the capture (7) plus the number of repeat units in the reporter (1) equals 8. The depiction relates to the diagram of FIG. 5 in that it shows the results attained in the analysis of a DNA sample containing an eight repeat unit target with a one repeat unit reporter.

Figure 7A:
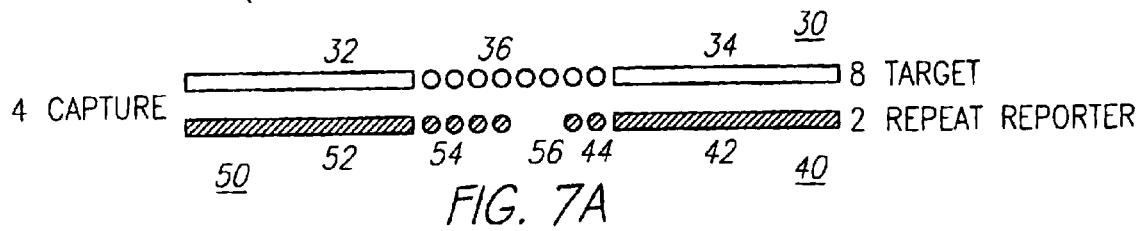
FIGS. 7A–7G show a diagrammatic view of a multiplex discrimination system, including a target having eight base repeat units, a reporter having two base repeat units, and a series of capture sequences including from four to ten repeat units in FIGS. 7A–7G, respectively.

FIGS. 7A through 7G are diagrammatic depictions of a multiplex system, such as a sandwich assay, in which the reporter includes two repeat units. This is in distinction to the assay of FIGS. 5A–G wherein the reporter included a single repeat unit. Again, for expository convenience, the numbering of earlier figures will be adopted to the extent of similarity. FIG. 7A shows a target 30 having a first unique flanking region 32 and a second unique flanking region 34. The reporter 40 includes a unique sequence region 42 and, in this example, two repeat units 44. The capture sequence 50 includes a capture unique sequence region 52 and 4 repeat units 54. Again, as a matter of nomenclature, the capture 50 may be referred to as a "5 capture", reflecting the terminology utilized in connection with the assay of FIGS. 5A–5G, namely those in which a reporter 40 having a single repeat unit 44 is utilized.

Figure 7B:
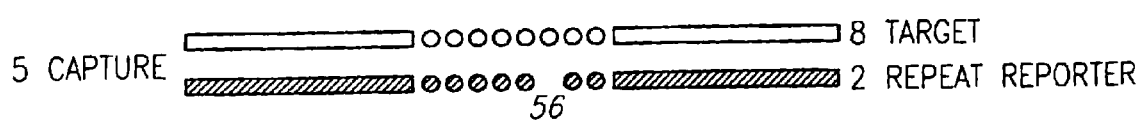

FIG. 7B shows a multiplex system wherein the capture 50 includes 5 base units 54. Each of the examples of FIGS. 7A and 7B include a gap 56.

Figure 7C:
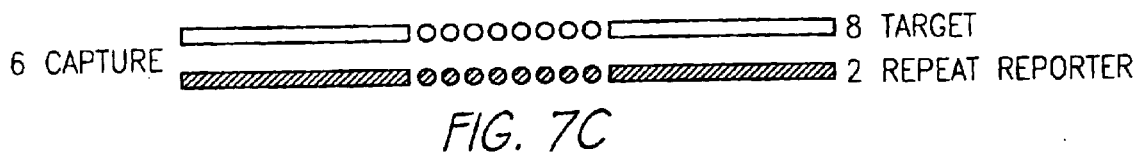

FIG. 7C shows a match condition in that the number of repeat units 36 in the target 30 is equal to the sum of the number of repeat units 54 in the capture 50 plus the repeat units 44 in the reporter 40 (6+2=8). FIG. 7C depicts the concordant test site in that the match condition exists. Note that the effective location of the concordant test site has shifted from FIG. 5D to FIG. 7C. This is a reflection of the change in the number of repeat units 44 in the reporter 40. Where a sequence or flight of unit incrementally longer captures 50 are utilized, a reporter 40 being one base unit 44 shorter or longer will shift the physical location of the concordant test site, such as in FIG. 6 from test site 26D to 26C when going from a reporter of one repeat unit 44 to a reporter 40 having two repeat units 44.

Figure 7D:
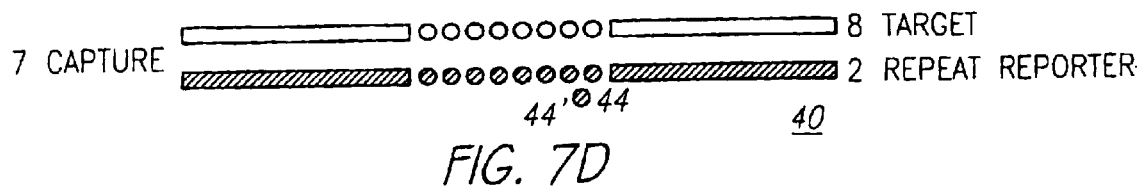
Figure 7E:
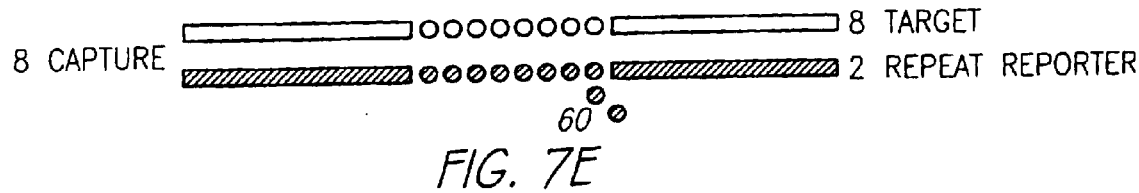
Figure 7F:
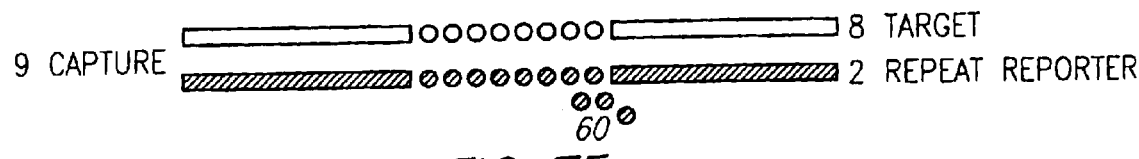
Figure 7G:
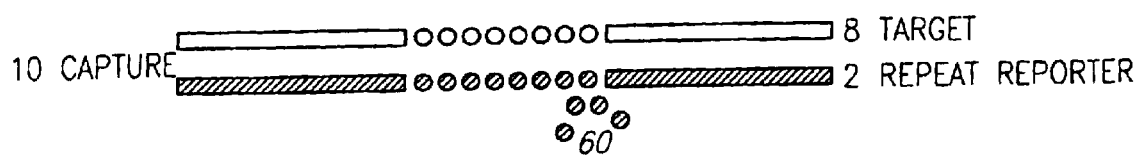

FIGS. 7B–7G show an overlap condition. In FIG. 7D, one repeat unit 44 of the reporter 40 is in a hybridized relationship with a repeat unit 36 of the target 30. A second repeat unit 44' of the reporter 40 is in a mismatched, overlap condition with the complex. FIG. 7E shows an overlap condition wherein repeat units 60 are in a non-hybridized condition with the target 30. FIGS. 7F and 7G also include mismatch arrangements including overlap wherein multiple repeat units 60 are in a non-hybridized condition with the target 30. The mismatch repeat units may either be those from the reporter 30 or from the capture 50, or a combination of both.

Figure 8:
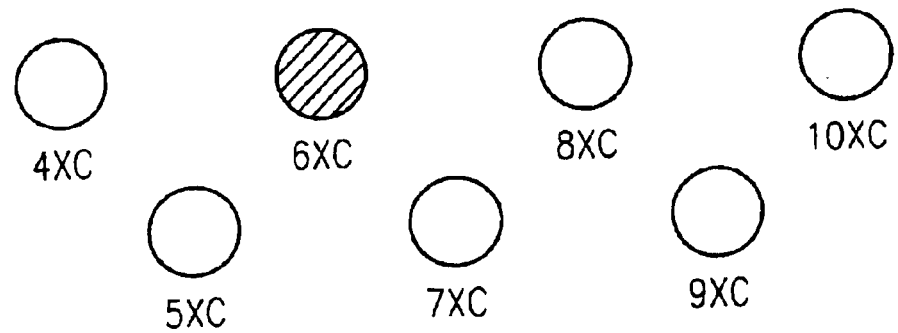
FIG. 8 shows a plan view of an array of test sites for a redundant assay with the concordant test depicted as shaded to represent the presence of hybridization complex.

FIG. 8 shows a plan view of an array of test sites for use in a multiplex assay, such as a sandwich assay. The concordant test site is determined to be at the site containing the 6 repeat unit capture. This assay depicts an assay done with a 2 repeat unit reporter, therefore one can determine that the target must contain 8 repeat units since at the concordant site, the number of repeat units in the capture (6) plus the number of repeat units in the reporter (2) equals 8. The depiction relates to the diagram of FIGS. 7A–7G in that it shows the results attained in the analysis of a DNA sample containing an eight repeat unit target with a two repeat unit reporter. In comparison with FIG. 6, one notes the change in the concordant test site location and confirmation of the target allele determination, when the target DNA is redundantly assayed with a second reporter oligonucleotide.

Figure 9A:
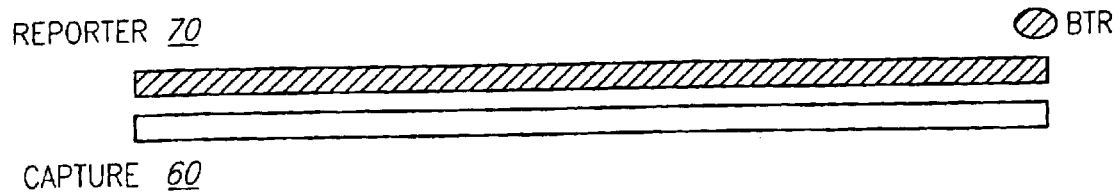
FIG. 9A shows a diagrammatic view of a target and hybridized reporter in a concordant condition.
Figure 9B:
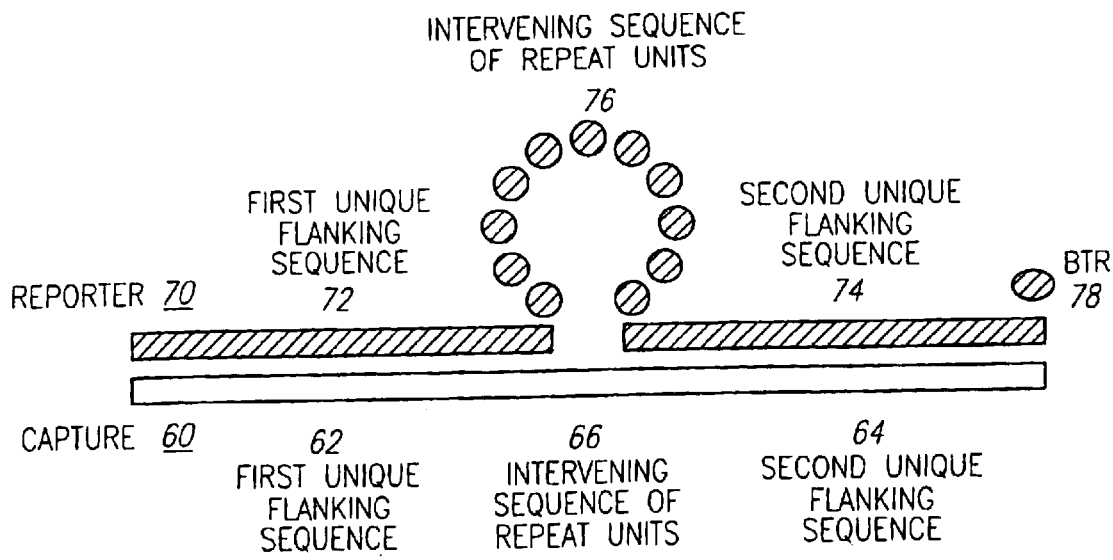
FIG. 9B shows a target and reporter in a discordant condition, namely in a loop condition.

FIG. 9A and FIG. 9B show diagrammatic views of a loopout embodiment of the invention. In the figures, a capture 60 includes a first unique flanking sequence 62, a second unique flanking sequence 64 and an intervening sequence of repeat units 66 comprising one or more repeat units. A reporter 70 includes a reporter first unique flanking sequence 72, a reporter second unique flanking sequence 74 and an intervening sequence of repeat units 76. The number of repeat units in the intervening sequence of repeat units 76 of the reporter 70 may be the same as or different than the number of repeat units in the intervening sequence of repeat units 66 of the capture 60. A reporter label 78 may be included.

Figure 10A:
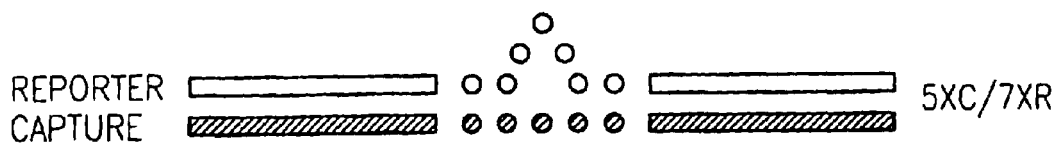
FIGS. 10A–10G depict multiplex discrimination in a loop out system wherein a target includes seven repeat units and the reporters include from five to eleven repeat units in FIGS. 10A–10G, respectively.
Figure 10B:
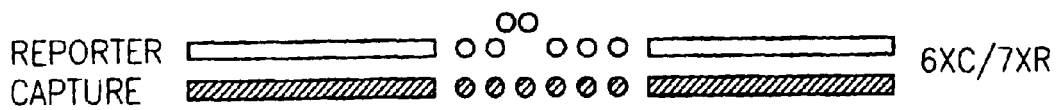
Figure 10C:
Figure 10D:
Figure 10E:
Figure 10F:
Figure 10G:

FIGS. 10A through 10G are depictions of multiplex systems having a variable length of repeat units. The numbering for FIGS. 7–10 will adopt that from FIGS. 9A and 9B to the extent practicable. In FIG. 10A, a capture 60 includes a first unique flanking sequence 62, a second unique flanking sequence 64 and an intervening sequence of repeat units 66 having 5 repeat units. The reporter 70 includes a reporter first unique flanking sequence 72, a reporter second unique flanking sequence 74 and a intervening sequence of repeat units, specifically, 7 repeat units. A mismatch or loopout condition exists given the different number of repeat units in the intervening sequences 66, 76. Similarly, in FIGS. 10B and 10D–10G, a mismatch or loopout condition exists. Each of the component figures includes 7 base repeat units in the reporter 70. A flight or sequence of monitonically increasing number of repeat units in the intervening sequence of repeat units 66 for the capture 60 is depicted. FIG. 10B includes 6 repeat units, which still results with a mismatch, loopout condition in FIG. 10B where the excess repeat units in the intervening sequence 76 of the reporter 70 are looped out. In each of FIGS. 10D–10G, the number or repeat units in the intervening sequence 66 in the capture 60 exceeds the number of repeat units in the intervening sequence 76 of the reporter. A loopout or mismatch condition then exists. In FIG. 10D, 8 repeat units exist within the intervening sequence of repeat units 64, which differs by one repeat unit from the number within the reporter intervening sequence of repeat units 76. In FIG. 10E, there are 9 repeat units in the intervening sequence of repeat units 64 in the capture 60. In FIG. 10F, there are 10 repeat units in the intervening sequence of repeat units 64 of the capture 60. In FIG. 10G there are 11 repeat units in the intervening sequence of repeat units 64 of the capture 60.

In one mode, the hybridization complex is labeled and the step of determining concordance and discordance includes detecting of the amounts of labeled hybridization complex at the test sites. The detection device and method may include, but is not limited to: optical imaging, electronic imaging, imaging with a CCD camera and integrated optical imaging. Further, the detection, either labeled or unlabeled, is quantified, which may include statistical analysis. The labeled portion of the complex may be the: target, capture, reporter or the hybridization complex in toto. Labeling may be by fluorescent labeling selected from the group of but not limited to: Bodipy Texas Red, Bodipy Far Red, Lucifer Yellow, Bodipy 630/650-X, Bodipy R6G-X and 5-CR 6G. Labeling may further be done by colormetric labeling, bioluminescent labeling and/or chemiluminescent labeling. Labeling further may include energy transfer between molecules in the hybridization complex by: perturbation analysis, quenching, electron transport between donor and acceptor molecules, the latter of which may be facilited by double stranded match hybridization complexes (See, e.g., Tom Meade and Faiz Kayyem, electron transport through DNA). Optionally, if the hybridization complex is unlabeled, detection may be accomplished by measurement of conductance differential between double stranded and non double stranded DNA (See, e.g., Tom Meade and Faiz Kayyem, electron transport through DNA). Further, direct detection may be achieved by porous silicon-based optical interferometry.

The label may be amplified, and may include for example branched or dendritic DNA. If the target DNA is purified, it may be unamplified or amplified. Further, if the purified target is amplified and the amplification is an exponential method, it my be, for example, PCR amplified DNA or SDA amplified DNA. Linear methods of DNA amplification such as rolling circle or transcriptional runoff may be used. Wherein target DNA is unpurified and unamplified or amplified, the amplification methods further consisting of PCR and SDA for exponential amplification and rolling circle or transcriptional runoff for linear amplification.

The target DNA may be from a source of tissue including but not limited to: hair, blood, skin, sputum fecal matter, semen, epithelial cells, endothelial cells, lymphocytes, red blood cells, crime scene evidence. The source of target DNA may include: normal tissue, diseased tissue, tumor tissue, plant material, animal material, mammals, humans, birds, fish, microbial material, xenobiotic material, viral material, bacterial material, and protozoan material.

Wherein the target material is from cloned organisms (Ian Wilmut, Roslyn Institute, Edinborough) to determine degree of identity and level of genetic drift.

Further, the source of the target material may include RNA. Further yet, the source of the target material may include mitochondrial DNA.

EXAMPLES

Example 1

Identification of TH01 Target DNA Alleles by the Sandwich Hybridization Method

The TH01 locus contains the tetranucleotide repeat (AATG) present in five to eleven copy-numbers in a non-coding region of the Human Tyrosine Hydroxylase gene (ref). This locus is one of many commonly used and accepted by the forensics community for DNA fingerprinting. FIG. 1 depicts data from an experiment designed to determine the identities of the alleles present in an unknown target DNA sample after analysis by the method described here.

A silicon chip was prepared by spin coating onto the top of the electrodes an organic layer of agarose mixed with streptavidin, thus forming the permeation layer that serves as the underlying foundation for DNA attachment (See e.g., U.S. application Ser. No. 08/271,882, filed Jul. 7, 1994, entitled "Methods for Electronic Stringency Control for Molecular Biological Analysis and Diagnostics", accord., Sosnowski et al., 1997, Proceedings of the National Academy of Science USA). This permeation layer is contiguous with the electrode on one side and contiguous with the buffer containing the analyte on the other. Capture DNA specific for each TH01 allele was then electronically addressed to individual sites on the spin coated chip, so that each test site is capable of detecting a different TH01 allele. Sequences for the capture oligos are listed in Table 1. The capture oligos were electronically addressed in 50 mM histidine buffer at its natural pH ~5.4, at a concentration of 500 nM. Pads were biased positive 5 at a time and a current source of +4.0 microamps ($\mu$A) was applied for 38 milliseconds (ms). The polarity of the field was then reversed and −4.0 ~ A was applied to the 5 pads for 25 ms. This cycle was repeated 500 times for a total electronic addressing time of ~30 seconds. Under these conditions, the biotin moiety of the capture oligo reacts with the streptavidin in the permeation layer over the activated test site to immobilize the capture oligo at that site.

A mix of complementary target DNA, composed of TH01 alleles 5 and 9 (Table 1), was then electronically hybridized to each of the sites containing addressed capture DNA. The electronic hybridization was done in low conductivity zwitterionic buffer at a temperature empirically determined to promote nonslippage hybridization. Due to the nature of electronic hybridization, specifically the low conductivity buffer (Edman, et al., Nucleic Acids Research, 1997), high stringency hybridization can be attained at lower temperatures than conventional nonelectronic hybridization. Experiments for TH01 analysis were usually performed at 34–42% C. The target DNA was electronically hybridized in 50 mM histidine buffer at its natural pH~5.4, at a concentration of 5–125 nM. The programmed electronic protocol included the following steps. Pads were biased positive 5 at a time and a current source of +4.0 microamps ($\mu$A) was applied for 19 milliseconds (ms). The polarity of the field was then reversed and −4.0 $\mu$A was applied to the same 5 pads for 12 ms. This biased-AC cycle was repeated 500 times for a total electronic addressing time of 30 seconds.

This experiment has also been done by passive, nonelectronic hybridization at high stringency conditions, but with much longer incubation times (50 mM NaPO$_4$ buffer, pH 7.0, 60% C, 30–60 minutes, results not shown).

The stringency of this hybridization step is critical due to the malleable nature of the tetranucleotide repeat complementary alignment. It is quite easy to obtain stable hybrids without aligning the flanking unique sequences, since the length of the repeat region is 20–44 bases. The out of register hybrids formed by insufficient stringency will not be accurately distinguished by any hybridization assay. High stringency hybridization can be attained at relatively low temperatures with electronic hybridization because of the low conductivity of the buffer and resulting low shielding of the repulsive negative charges on the DNA backbone. Electronic concentration of DNA overcomes these repulsive effects while maintaining highly stringent hybridization conditions.

Reporter DNA, 1 Repeat Unit (FIG. 13, 500 nM in 50 mM NaPO4, 500 mM NaCl, pH 7.0) was then passively hybridized to the capture-target complexes formed by the above steps. Reporter hybridization was most stable at those test sites where the target directs hybridization to provide a juxtaposition of the terminal nucleotides of the capture and reporter oligo. This additional stability is due to the base stacking of the terminal nucleotides. This juxtaposition will be 5'–3' or 3'–5' depending on the position of the attachment chemistry on the capture oligo. Unstable configurations would be a four base (or greater) gap between the capture and reporter or a four base (or greater) overlap of the capture and reporter (See, e.g., FIGS. 3A–3C, and 5A–5G).

After reporter hybridization, the DNA loaded chip is washed several times with 50 mM NaPO$_{4, pH}$ 7.0 at ambient temperature. The temperature of the hybridized organo-chip is then increased to 30% C and fluorescence levels at each test site are recorded at one minute time intervals. The fluorescent values are digitized by a computer program (IP Lab) as mean pixel intensity. A specific area over each pad is selected, and the pixel intensity for each site is stored for analysis. The histogram in FIG. 1 displays the mean pixel intensity at each test site immediately after the denaturation step is complete.

Figure 11:
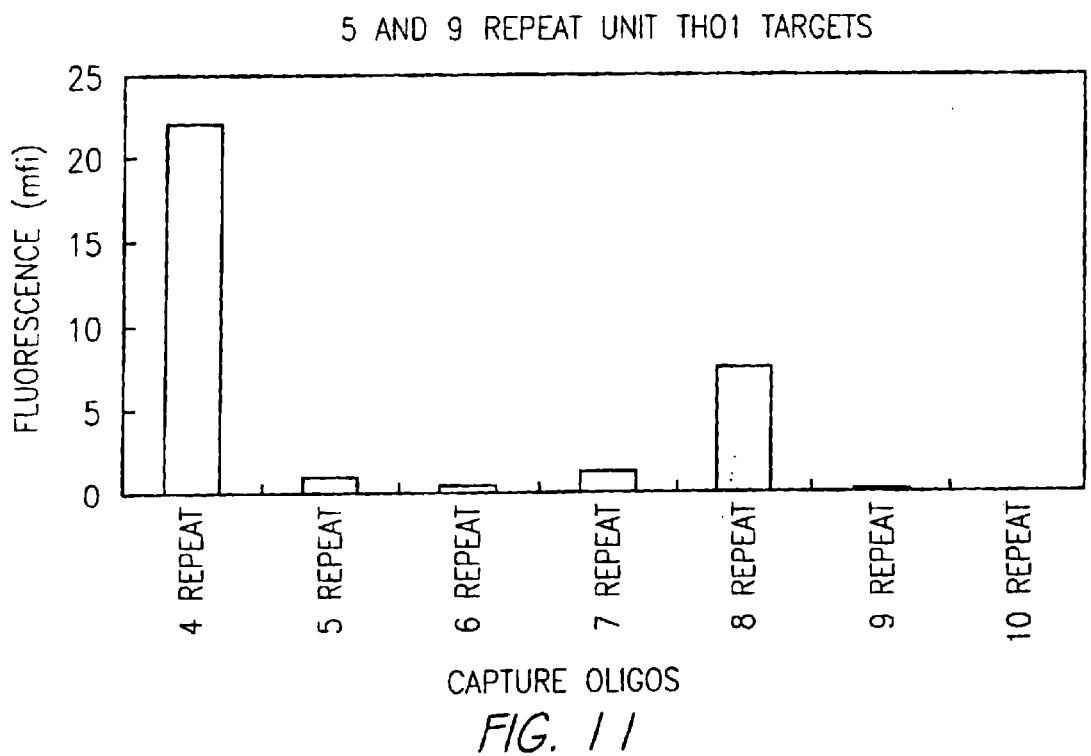
FIG. 11 is a graph of fluorescence (MFI) as a function of capture oligo repeat unit number in the identification of TH01 target DNA alleles by the sandwich hybridization method.

FIG. 11 shows a graph of the fluorescence as a function of number of repeat units. These results show that a heterozygous mix of TH01 DNA can be resolved into match (concordant) and mismatch (discordant) hybrids, with the match hybrids representing the identity of the alleles present in the DNA sample. All possible homozygote and heterozygote TH01 STR allelic combinations (5+6, 5+7, 5+8 etc.) have been analyzed by the chip format, such as shown in FIGS. 1A and 1B, with similar excellent levels of discrimination among alleles.

Example 2

Reanalysis of Target DNA with Redundant Reporters

Figure 12:
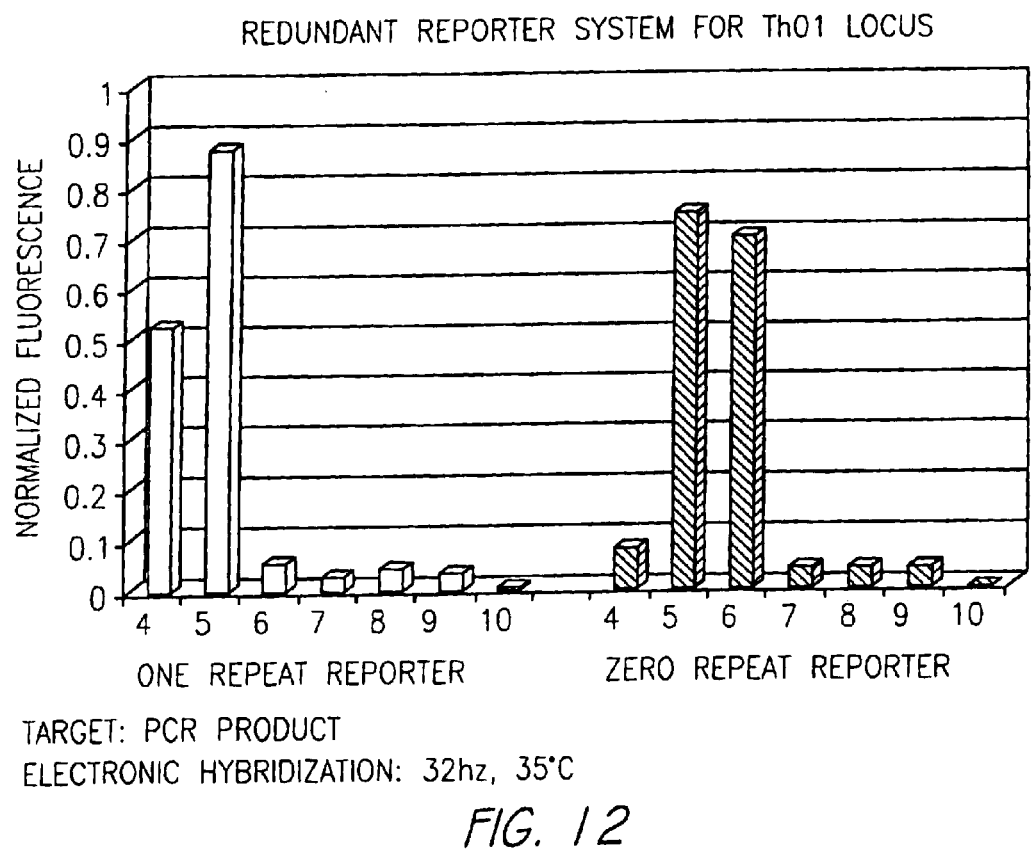
FIG. 12 is a graph of normalized fluorescence as a function of the number of repeat units in the capture sequence, where the reporter includes one repeat unit (left-hand side) and includes zero repeat units (right-hand side) showing a redundant reporter system for the TH01 locus.

One Repeat Unit reporter was denatured from the match sites of the chip described in the preceding example by increasing the temperature ~50% C, conditions which do not denature the target from the capture. This chip was then rehybridized with the Zero Repeat Unit reporter (See, e.g., FIG. 5). This shifts the position of stable sandwich complexes from the 4 and 5 sites (See, FIG. 12, left hand side, One Repeat Unit Reporter) to the 5 and 6 sites (FIG. 12, right hand side, Zero Repeat Unit Reporter). Using the formula that the number of repeat units in the capture plus the number of repeat units in the reporter equals the number of repeat units in the target, we find that the target DNA in this case had a heterozygous mix of the 5 and 6 alleles of TH01. The reanalysis confirms the identity of the alleles present in the target DNA with a second oligo sequence. This redundant analysis increases the significance of the assay result since it is essentially a new interrogation of the target DNA with an oligo that has a different sequence. Using a different sequence reduces the possibility of artifactual results due to oligo secondary structure or other sequence-related anomalies. Therefore, the use of additional oligos for target analysis reduces the possibility of false positive and/or negative results.

The above protocol was repeated with the Two Repeat Unit reporter (See, e.g., FIGS. 7A–7G), to shift the location of stable match hybrids to a third test site. This additional reiteration of the STR analysis further strengthens the robustness of the assay.

Example 3

Selection and/or Modifications of Terminal Nucleotides to

Increase Base Stacking Effect

Base stacking is dependent on the interactions of the ring structure of one base with the base ring of its nearest neighbor. The strength of this interaction depends on the type of rings involved, as determined empirically. While applicants do not wish to be bound by any theory, among the possible theoretical explanations for this phenemon are the number electrons available between the two bases to participate in pi bond interactions and the efficiency of different base combinations to exclude water from the interior of the helix, thereby increasing entropy, Although the above models are consistent with current data, the possible mechanisms of stacking interactions are not limited to these concepts.

It has also been observed that modification of bases involved in base stacking interactions can strengthen pi bonding, or stacking, between them. As one might predict from the models described above, these modifications provide more electrons for use in Pi bonding and/or to increase the surface area of the rings thereby increasing the area of hydrophobicity between the stacked bases.

Figure 14:
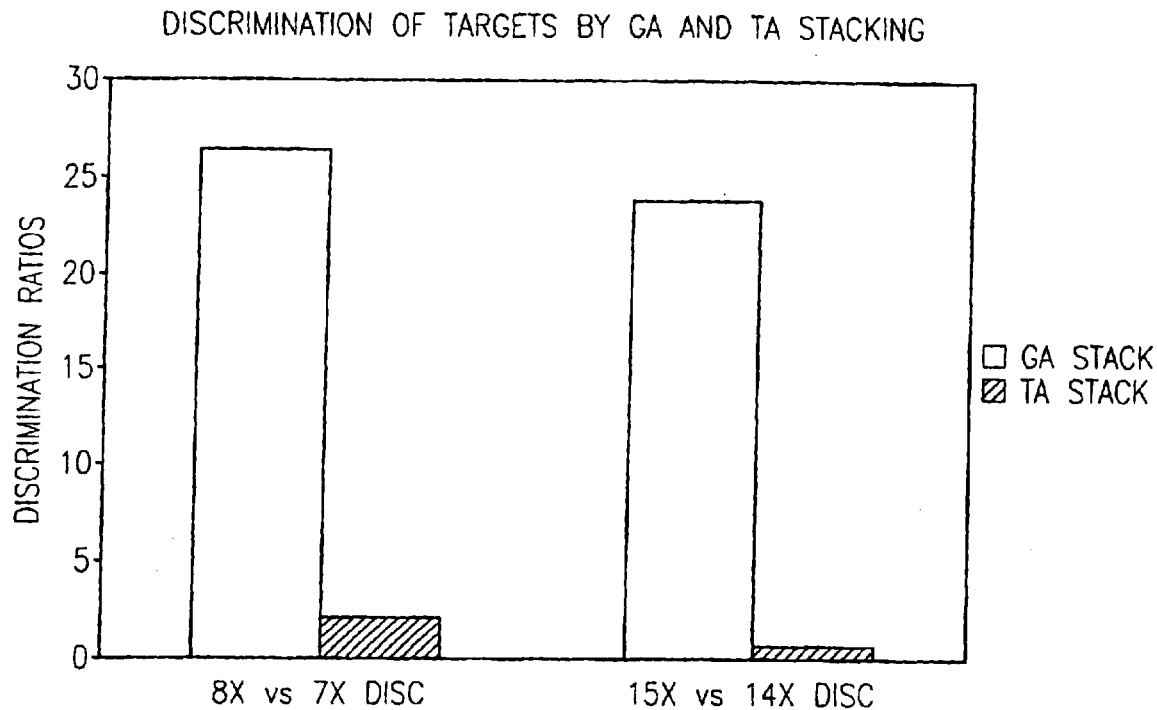
FIG. 14 is a graph of discrimination ratios as a function of G-A stacking compared to T-A stacking in the paired left, right or graphs, respectively, for an eight x versus seven x discrimination (left-hand bars) and for a fifteen x versus fourteen x discrimination (right-hands bars) showing discrimination of targets by G-A and T-A stacking.
Figure 15:
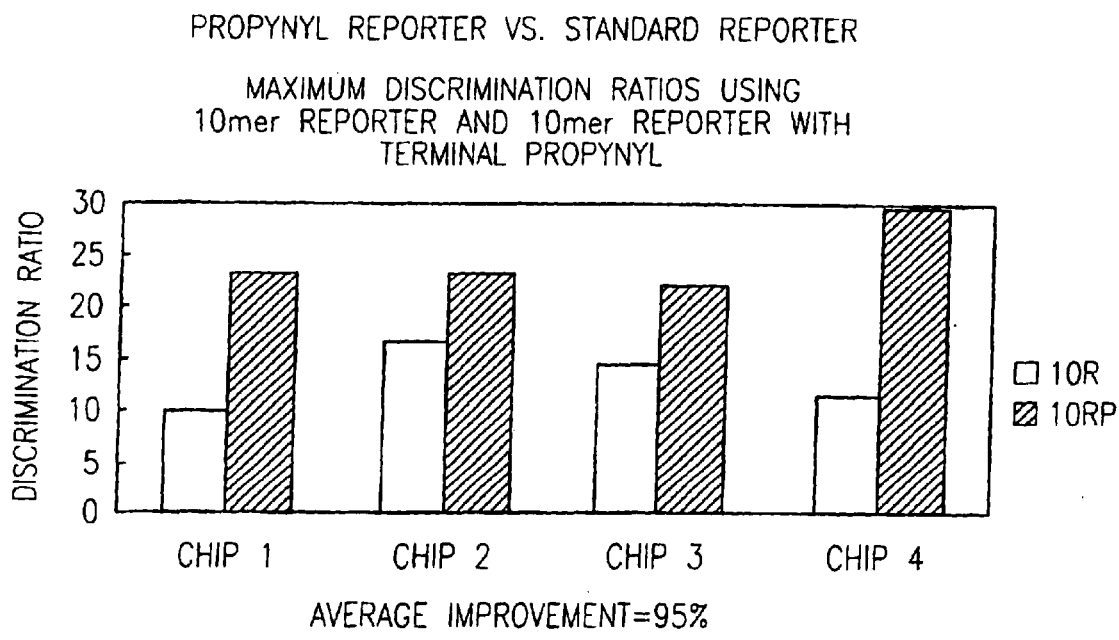
FIG. 15 is a graph of discrimination ratio showing four couplets for chip one through chip four, respectively, showing maximum discrimination ratios utilizing a ten mer reporter (a left bar in couplet) and ten mer reporter with terminal propynyl group (right bar in couplet).

FIG. 14 demonstrates an example of these models as applied to this invention. Initial experiments with the CSF1PO locus used an A and T as the terminal nucleotides to provide discriminating base stacking. References indicate that A-T base stacking interactions are the least stable of all nucleotide combinations. Therefore we altered the design of the capture and reporter oligos to make G and A the terminal nucleotides, since this is reported to be a much more stable conformation. The experiment was done by the method described in Example 1, with the exception that the locus examined was CSF1PO. To compare the base stacking contributions of different juxtaposed contiguous terminal nucleotides, an additional set of CSF1PO capture and reporter were designed to change the terminal nucleotides from T-A to G-A. FIG. 15 compares discrimination of match from mismatch hybrids containing either A-T or G-A terminal nucleotides. The results are displayed as discrimination ratios, that is the Mean Fluorescent Intensity (MFI) of the concordant site divided by the average MFI of the discordant sites. One sees that the Discrimination Ratios increase from about 2.5 to about 25 when G-A terminal nucleotides are used rather than T-A terminal nucleotides.

These data demonstrate that this system can be modulated in a manner predicted by base stacking theory, as well as earlier observations, thereby underscoring the mechanism of the invention as dependent on Pi bonding between juxtaposed bases.

In addition to taking advantage of the naturally selected base stacking interactions, it may be predicted that base modifications which increase the number of electrons in the ring or enlarge the hybdrophobic area would also increase discrimination of match from mismatch hybrids. This was tested by synthesizing TH01 reporter oligos whose 5' terminal nucleotide contained a propynyl group attached to the ring of the base. This modification would be predicted to increase base stacking by either of the increased electronorhydrophobicity models described above. FIG. 15 shows match/mismatch results in a direct comparison of a TH01 reporter with or without a propynyl-modified terminal base. This experiment was done as described in Example 1 with the TH01 locus. The data are again presented as discrimination ratios. In 4 separate experiments, enhanced stability is observed in complexes containing reporters with propynyl-modified reporters. The average increase in discrimination ratios was 95%. The results show that again, this system can be manipulated in a predictable fashion. This concept could be carried further by adding other analogs such as methyl of cholesterol groups. Techniques for adding these types of modifications are known (e.g. Gryaznov).

These modifications could be used to further stabilize the binding of the reporter to the concordant by linking the modifying molecules together. One example of this is taught by Gryaznov in the use of cholesterol at both terminal nuclei and the addition of a cholesterol binding molecule, such as low density lipoprotein (LDL). This would result in a complex at the concordant site which consists of target, cholesterol-modified capture, cholesterol-modified reporter and LDL.

Example 4

Hybridization Detection of TPOX alleles

The TPOX locus contains the tetranucleotide repeat (AATG) present in six to thirteen copy-numbers in a non-coding region of the Human Thyroid Peroxidase gene (See, e.g., Anbach et al., 1996, Advanced in Forensic Haemogenetics). This locus is also one of many commonly used and accepted by the forensics community for DNA fingerprinting. The sequences are provided in FIG. 17.

Figure 16:
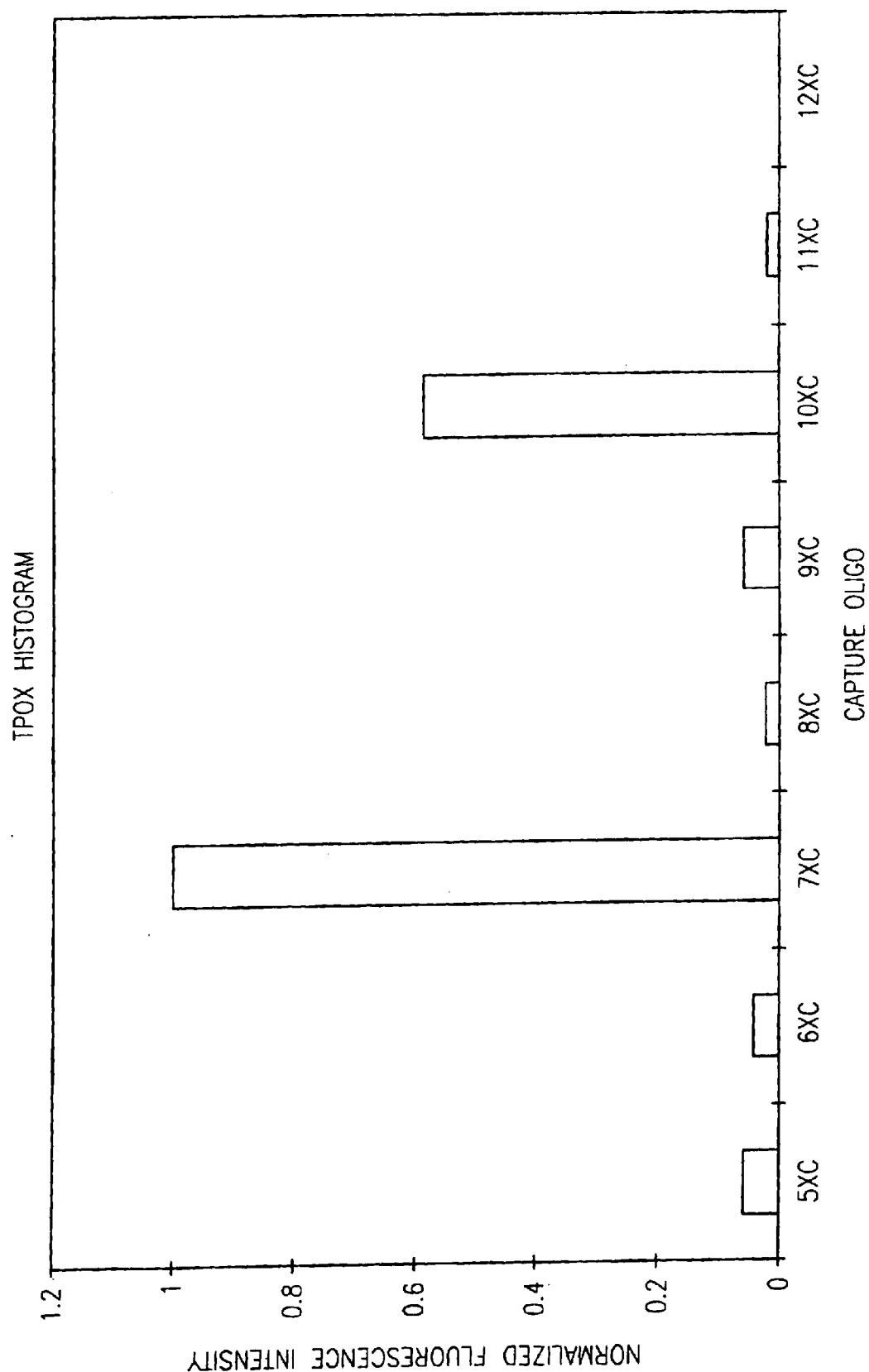
FIG. 16 is a graph of normalized fluorescence intensity as a function of capture oligo, in a heteroxygeous TPOX locus.

FIG. 16 depicts data from an experiment where target DNA containing the TPOX 8 and 11 alleles was analyzed by a procedure nearly identical to that described in Example 1. Oligo capture DNA containing all allelic possibilities was electronically addressed to individual sites on the chip. A mix of complementary target DNA, composed of TPOX alleles with 8 and 11 STRs, was then electronically hybridized to each of the pads containing addressed capture DNA. The conditions for electronic hybridization were the same as those outlined in Example 1. One Repeat Unit Reporter oligo was then passively hybridized to the array and treated in the manner of the TH01 example. FIG. 16 shows a stable hybridization complex at the test sites containing capture oligos with 7 and 10 repeat units. Since the reporter oligo has one repeat unit, the target DNA can be identified as having 8 and 11 repeat units.

The results show that a mix of TPOX 8 and 11 STR DNA can be unequivocally discriminated from all mismatches. Further, all other homozygous and heterologous TPOX combinations analyzed yield comparable discrimination.

Example 5

Hybridization discrimination of CSF1PO alleles

Figure 18:
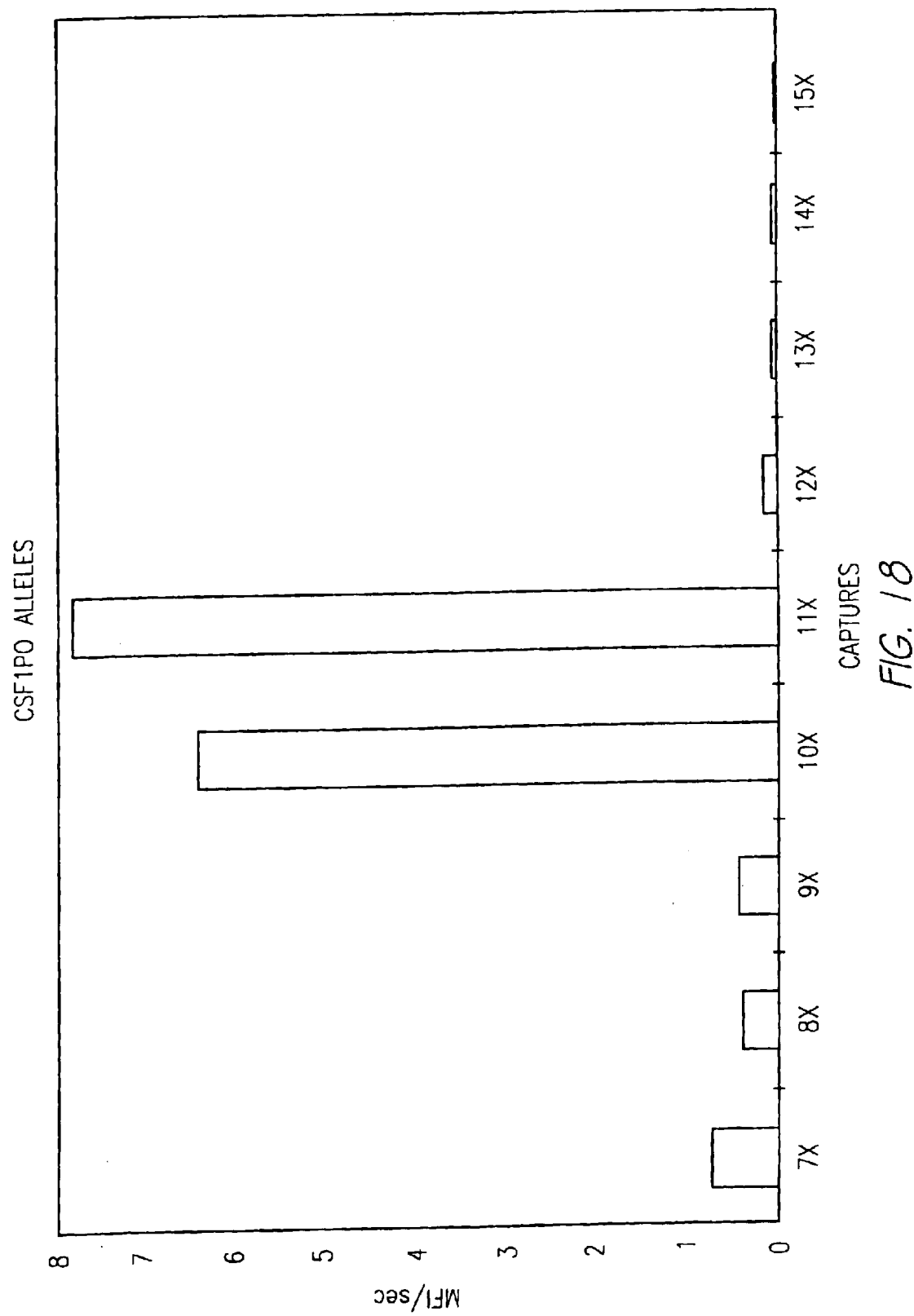
FIG. 18 is a graph of fluorescence intensity (MFI/sec) as a function of number of capture repeat units for hybridization discrimination of CSF1PON alleles.

Capture oligos containing CSF1PO alleles 7 through 15 (FIG. 19) inclusive were electronically addressed to representative sites as previously described. Target DNA containing CSF1PO 11 and 12 alleles (FIG. 19) was then electronically hybridized to each of the sites. The CSF1PO one repeat unit reporter (FIG. 19) was then. Denaturation of the reporter was done at 30% C. FIG. 18 shows the mean pixel intensity at various capture sites after the assay, demonstrating the ability of the assay to correctly discriminate the alleles present in the target sample. The experiment was done as described in Example 1.

Example 6

TH01/TPOX Multiplex Analysis

Locus-allele specific capture oligos were individually addressed to different sites on a single chip. The DNA chip containing capture oligos was then hybridized with a mixture of TH01 and TPOX target DNA containing heterozygote alleles. The chip was then washed and analyzed by the hybridization assay of the form described previously. The above steps were performed as described in Example 1. Relative fluorescent levels were used to determine whether sites contain concordant or discordant DNA hybrid complexes. Both reporters used contained one repeat unit.

Figure 20:
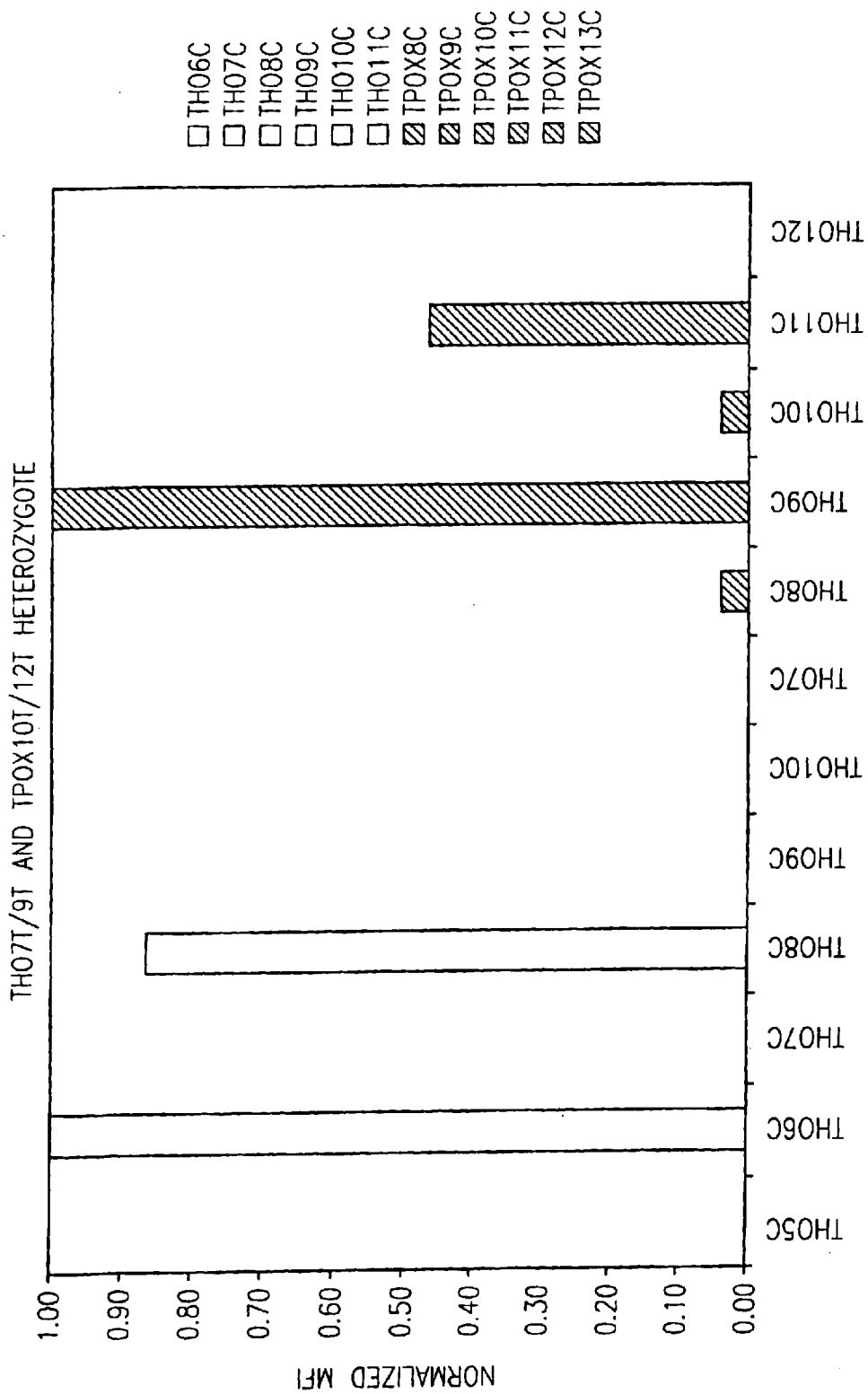
FIG. 20 is a graph of normalized intensity as a function of repeat unit number in the capture sequence in a THO1/TPOX multiplex analysis.

The results of FIG. 20 showed that under the assay conditions, 7 and 9 STR alleles of TH01 hybridized very well with their cognitive capture sites. Hybridization to other capture alleles was not detectable (5x, 7x, 9x and 10x), indicating an excellent discrimination of TH01 7/9 heterozygote. For the TPOX locus, we also obtained a good matched capture/target interaction (sites 9x and 11x). Further, the stability of the discordant hybridization complexes formed with the 10 and 12 STR targets was so low that the complexes were either undetectable (7xc and 12xc), or low enough to yield a discrimination ratio of 15 fold or higher (10xc and 8xc respectively), resulting in easy discrimination of TPOX 10/12 heterozygote target.

Example 7

Identification of STR Alleles in Double Stranded PCR-amplified DNA

This experiment was done to determine the utility of the current invention as applied to interrogation of double-stranded DNA generated by PCR amplification. FIG. 6 provides an example of the ability of our system to accurately identify PCR generated targets.

The TPOX 1 locus was PCR amplified using a genomic template from the K562 cell line following standard conditions outlined in the Promega STR User's manual (3). The genotype of K562 is heterozygous for the 8 and 9 repeat alleles. Following amplification the amplicon was denatured at 95% C and hybridized to a Nanogen APEX chip. As previously discussed, the chip had capture probes unique for PCR products containing each number of repeat length.

The technical aspects of this experiment were identical to those described in Example 1 and 4, with the exception of the use of double-stranded, PCR amplified DNA as the target.

Figure 21:
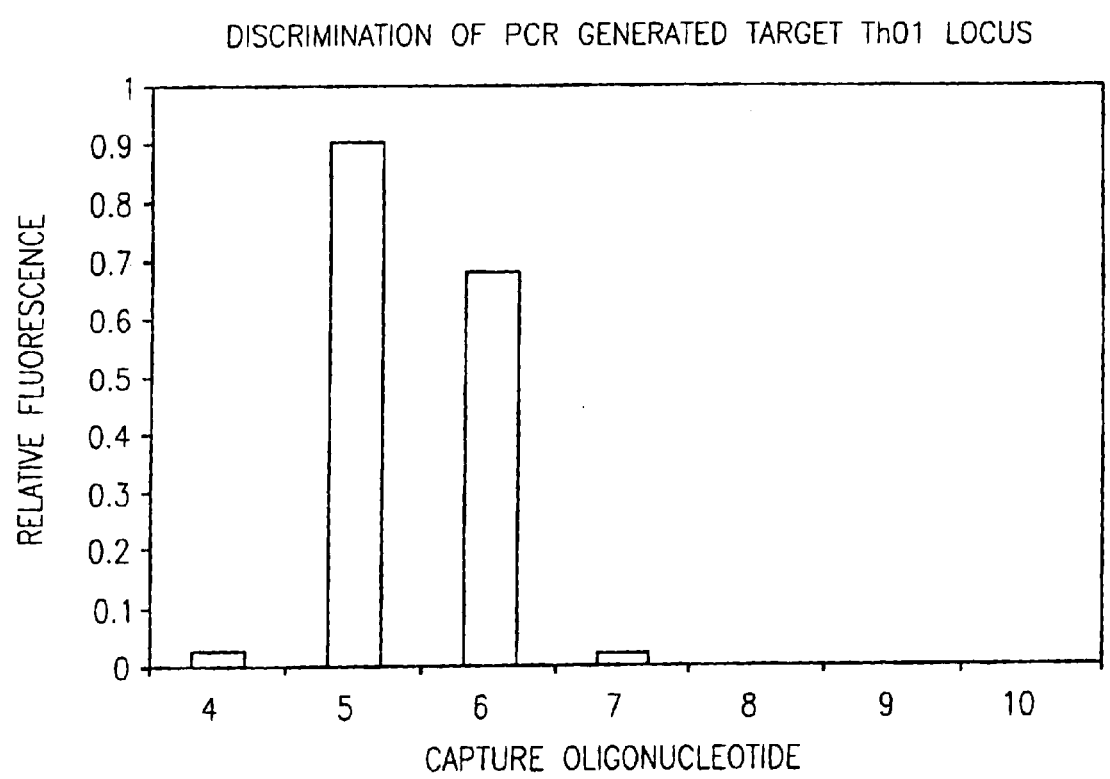
FIG. 21 is a graph of relative fluorescence as a function of repeat unit number in the capture oligonucleotide in a system for the identification of repeat unit alleles in double stranded polymers chain reaction (PCR) amplified DNA including the target TH01 locus.

FIG. 21 shows the relative amount of signal present on the positive (8C, 9C match) and negative (7C, 10C mismatch)

after the experiment has been performed. As seen in example 4 the level of discrimination attainable ranges from 20-fold to infinite. Similar results have been obtained using CSF1 and TH01 from both K562 control DNA and genomic DNA isolated from anonymous donors. These results suggest that the current invention is generally applicable to all double-stranded DNA, whether amplified by PCR or other technology, including the potential for analysis of unamplified DNA.

Example 8

Multivariant Detection

In the examples listed previously, detection has been accomplished by direct fluorescent labeling of the reporter or reporter/target DNA. One embodiment would be fluorescence perturbation where quencher and reporter chromophores are positioned proximal to each other such that fluorescence is quenched. See, e.g., (Methods for Hybridization Analysis Utilizing Electrically Controlled Hybridization and Methods For Electronic Fluorescent Perturbation for Analysis and Electronic Perturbation Catalysis for Synthesis), all incorporated by reference as if fully set forth herein.

Oligo synthesis and conjugation methods and materials are commonly practiced. In brief, the capture probe would have attachment moiety, such as biotin, at one end and a chromophore at the distal terminus or the terminus which extends into the STR region. During DNA synthesis linker arms or spacers would be incorporated at the appropriate location internally or at the terminus. These linker arms would have a functional group to which chromophores could later be conjugated, such as amino linker and succinimidyl ester chromophore. The reporter probe would have a different chromophore incorporated in the same manner, at the end which extends into the STR region. Thus, in the presence of target the capture and reporter probes would hybridize and position the chromophores proximal to one another. The distance between the chromophores would be determined by the spacer length and where the chromophore was attached to the DNA, via the base, backbone, or sugar.

Example 9

Target-Dependent Ligation of Capture and Reporter

An additional embodiment of this invention would be to further stabilize the attachment of the reporter to the concordant test site by ligating the reporter to the preattached capture. This would result in a covalent bond between the capture and the reporter with the capture being held at the site by biotin-streptavidin interaction.

The critical part of this embodiment would be to accomplish the ligation in a selective manner, maintaining the ability to discriminate match from mismatch hybrids. This could be done by careful maintenance of hybridization stringency, by electronic or conventional methods.

Ligation could be achieved enzymatic (Maniatis et al., Molecular Cloning, a Laboratory Manual, 1982) or chemical methods (Gryaznov, Nucleic Acids Research, 1994). Selection of the method could be determined by the kinetics involved with the specific type of reaction as well as the overall efficiency of taking a particular method into a product.

Example 10

Discriminating Match from Mismatch/Gap and Mismatch/Overlap

Figure 22A:
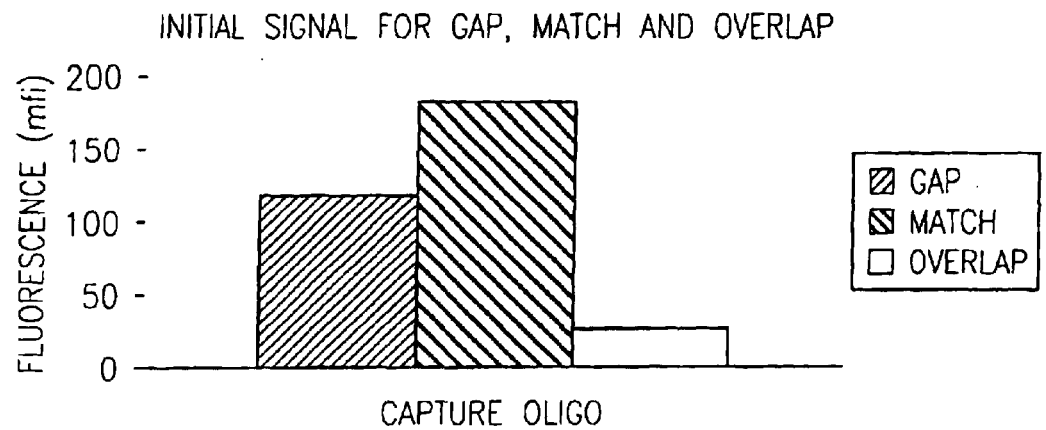
FIGS. 22A, 22B and 22C are graphs of the fluorescence (MFI) as a function of capture oligonucleotide having a gap (leftmost bar in triplet), match (center bar in triplet) or overlap (right bar in triplet) for the initial signal, for the signal after three minutes of denaturation and for the signal after ten minutes of denaturation for FIGS. 22A through 22C, respectively.
Figure 22B:
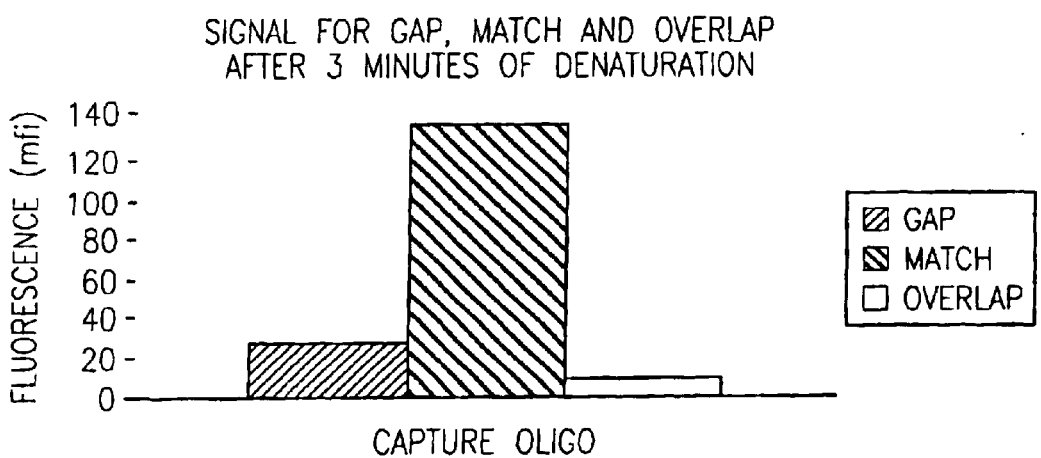
Figure 22C:
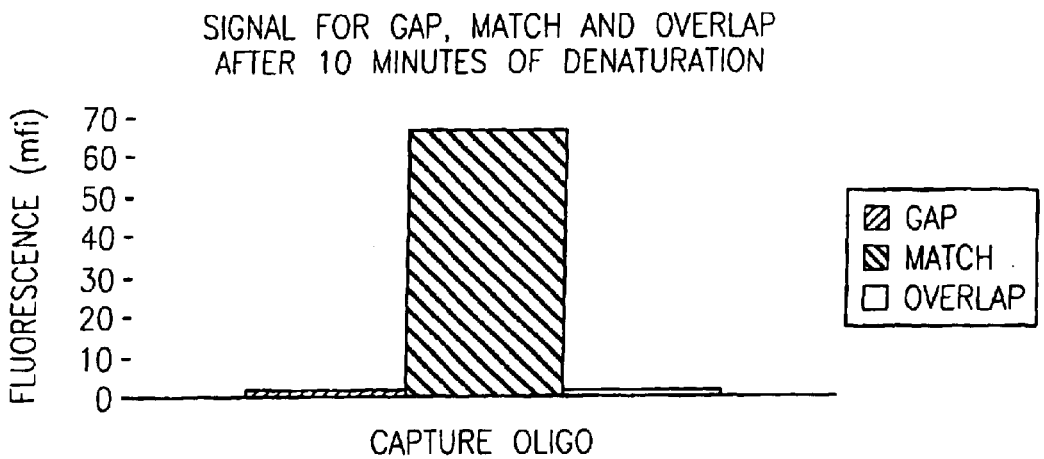

The ability of the system to discriminate not only match from mismatch hybrids, but also to discern between the two types of mismatches, gap and overlap increases the utility of the method. FIGS. 22A, 22B and 22C show graphics of fluorescence intensity for a gap, match and overlap condition (bar charts from left to right), for the initial signal (FIG. 22A) after three minutes of denaturation (FIG. 22B) and after ten minutes of denaturation (FIG. 22C). This feature of the technology provides additional information about the target DNA, that is, information regarding all three types of possible hybrids. This additional information can be used in several ways.

First, it may be possible to reduce the number of pads required for accurate identification of target DNA by taking advantage of this feature. FIG. 23 shows the potential for this feature in use with the TH01 locus. It predicts that correct identification of all TH01 alleles can be achieved with a set of capture oligos which have five, seven and nine repeat units in combination with the one repeat unit reporter TH01 locus. This reduces the required number of analytical test sites from seven to three. This feature, when combined with the ability to do redundant reporters, could greatly reduce the number of pads required for the analysis of a set of loci for statistically significant genotyping. Currently this level is approximately 10 loci. The beneficial effect of this would be to permit more loci on a single chip, and therefore with larger arrays, the ability to assay multiple individuals on the same chip thereby reducing the cost of the assay. This would be especially useful for high throughput processing, as will be required for the STR databasing of felons currently under way.

Even without a reduction in the number of test sites needed to assay STR alleles, the additional information gained from distinguishing gap mismatch from overlap mismatch will aid in the accuracy of the assay. Any additional information could be incorporated into the ultimate statistical analysis of the data to provide an answer which has a higher probability of being accurate.

Example 11

Determination of STR Allelic Identity of Target DNA by Loopout Analysis

In another embodiment of STR allele discrimination by hybridization, we have demonstrated that a different oligonucleotide system can be used. This method, designated the loopout system, is outlined in FIGS. 9A and 9B, and FIGS. 10A–10G. It is evident from the drawing that this is an alternative to the sandwich method of identifying alleles in a matrix. The loopout system uses an array of capture oligos which are distributed in a similar manner to the sandwich format. The structure of the capture oligos differs from ones in the sandwich format by the presence of locus-specific unique sequence flanking both ends of the repeat region. Also, the target DNA is labeled and serves as the reporter molecule. The target can be labeled during amplification by using a PCR primer which is fluorescent (or contains any other suitable molecular adaptation for detection).

Figure 24:
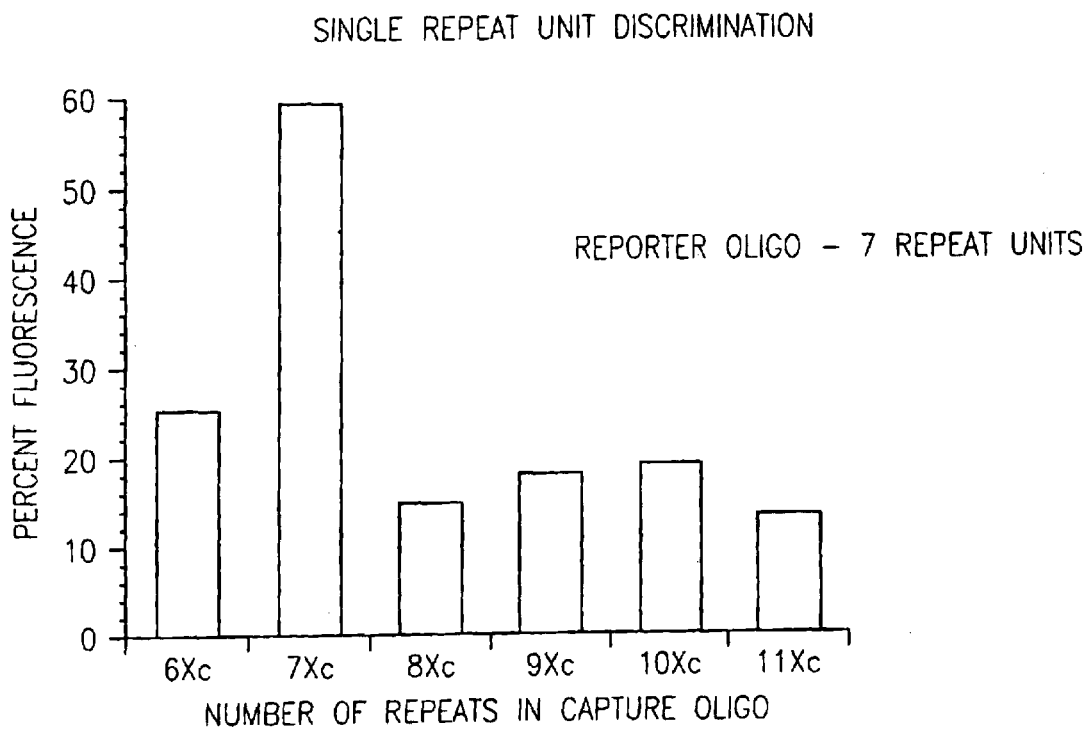
FIG. 24 is a graph of percentage fluorescence as a function of number of repeat units in the capture sequence for a determination of the nature and number of repeat units in allelic identity of target DNA utilizing the loop out analysis.

In practice, loopout capture oligos which are specific to different alleles of a locus are arrayed in a matrix such that individual test sites represent different alleles (See, e.g., FIG. 6). Actual test results are shown in FIG. 24. Labeled target oligo is then stringently hybridized under electronic conditions to the entire array. The test site with the most stable hybrids will be concordant with the allelic identity of the target DNA. Determining the position of the stable hybrids (and therefore the allele-specific capture oligo attached to it) identifies the alleles represent in the target DNA. Hybrids formed between capture and reporter oligos which have the same number of repeat units are matched. It may also be said that this test site is concordant with the identity of the target allele. Test sites which are discordant or contain an unequal number of repeat units between the capture and the target, will form a hybrid with a loop in either the target or capture DNA (See, e.g., FIGS. 10A, 10B and 10D–10G). Discordant sites which have captures with fewer repeat units than the target will yield hybrids with loops in the These hybrids will be inherently less stable than the match hybrids. Therefore denaturation by electronic stringency control will discriminate stable from less stable hybrids indicating the sites of concordancy, and based upon the knowledge of the probes present at those sites, enable the user to determine the number of repeat units in the target DNA.

Example 12

Detection of Microvariant Allele TH01 9.3

As STR's become more widely used, deviations within the repeat regions are being discovered with greater frequency. This can be troublesome to conventional size fractionation methods since the margin for discrimination goes from four bases down to one base. This is in the case of an insertion or deletion mutations. For transitional or transversional mutations, the size of the allele doesn't change, even though the sequence has become altered.

Both these classes of mutations, insertion/deletion and transitional/transversional can be readily detected by our technology. This is primarily due to the fact that Nanogen's approach is a hybridization based assay rather than a sizing method. Therefore combining terminal nucleotide base stacking with single nucleotide polymorphism provides a powerful discriminatory tool.

One well known STR microvariant is the TH01 9.3 allele. It is important because it is present in a significant portion of the Caucasian population. The assay for the 9.3 microvariant was essentially the same as the normal STR alleles but required special capture and reporter oligo design. The capture oligo contains only three repeat units (3ru, FIG. 13). This is because the single base deletion is between repeat units 6 and 3 on the target strand. TH01 9.3 target DNA binding to the capture will be less stable at capture sites containing greater than three repeat units because there will be a frame-shift in the repeat region of 9.3. The reporter oligo (Microvar 9.3, FIG. 13) has been designed so that it will bind most stably to the repeat unit region containing the deletion. Additionally, the capture oligo has been designed so that target directed base stacking of the capture and reporter DNA will occur only at the 3ru test site. FIG. 25 shows a detailed sequence alignment of the capture and reporter oligonucleotides used to detect the TH01 9.3 microvariant. The numbering in the drawing is consistent with that found in FIG. 4C, with the addition of sequence 45 which is complementary to the partial repeat unit which constitutes the microvariant. This particular microvariant reporter has no second unique flanking sequence 42. This is necessary for analysis of TH01 9.3 allele not be a feature of other microvariant-specific reporters. It is evident from this drawing in the hybridization complex which is concordant for the TH01 9.3 allele, there exists sequence complementarity between the target and reporter DNA as well as base stacking between the capture and reporter oligonucleotides. FIG. 26 shows the results of an assay of PCR amplified DNA from an individual homozygote for the TH01 allele.

Although the foregoing invention has been described in some detail by way of illustration and example for purposes of clarity and understanding, it may be readily apparent to those of ordinary skill in the art in light of the teachings of this invention that certain changes and modifications may be made thereto without departing from the spirit or scope of the appended claims.

We claim:

1. A method for determining the nature of a genetic variant in a nucleic acid target, comprising the steps of:
   providing a plurality of hybridization complex assays on a test device, where the hybridization complex comprises:
      a nucleic acid target containing a genetic variant nucleic acid sequence,
      a capture probe having a selected sequence complementary to a first target sequence, and
      a reporter probe having a selected sequence complementary to a different portion of the same target strand,
      wherein the reporter probe and capture probe form a hybridization complex with the target such that the termini of the capture and reporter are juxtaposed, and
   selecting the capture probe and reporter probe from a plurality of options, such that the juxtaposed termini are stabilized through base stacking and the energy difference between a concordant assay and a discordant assay is increased.

2. The method of claim 1 such that the base-stacking stabilization between the juxtaposed termini is maximized within a concordant hybridization complex.

3. The method of claim 1 such that the base-stacking stabilization between the juxtaposed termini is minimized within a discordant hybridization complex.

4. The method of claim 1 such that the differential base-stacking stabilization between the juxtaposed termini is maximized for a discordant and concordant hybridization complex.

5. The method of claim 1 wherein the genetic variant is immediately adjacent the termini.

6. The method of claim 1 wherein the genetic variant is one base removed from the termini.

7. The method of claim 1 wherein the genetic variant is two or more bases removed from the termini.

8. The method of claim 1 wherein the base-stacking is maximized by selection of the terminal bases.

9. The method of claim 1 wherein the base-stacking is maximized by selection of the position of the genetic variant relative to the juxtaposed termini.

10. The method of claim 1 wherein the base-stacking is maximized by selection of complementary sequences.

11. The method of claim 1 wherein the base-stacking is maximized by selection of the terminal bases and complementary sequences.

12. The method of claim 1 wherein the base-stacking is maximized by selection of the terminal bases, complementary sequences and position of the genetic variant relative to the juxtaposed termini.

13. The method of claim 1 for determining the nature of a genetic variant wherein the test device includes a plurality of test sites.

14. The method of claim 13 for determining the nature of a genetic variant wherein a test site includes a permeation layer disposed adjacent the microelectrode.

15. The method of claim 1 or determining the nature of a genetic variant wherein two different hybridization complexes are distinguished at a single site with distinguishable reporters.

16. The method of claim 1 for determining the nature of a genetic variant wherein two different hybridization complexes are distinguished at multiple sites with different reporters.

17. The method of claim 1 or determining the nature of a genetic variant wherein the variant constitutes the number of repetitive DNA sequences.

18. The method of claim 1 wherein the genetic variants include deletions.

19. The method of claim 1 wherein the genetic variants include insertions.

20. The method of claim 1 wherein the genetic variants include transitions.

21. The method of claim 1 wherein the genetic variants include transversions.

22. The method of claim 1 wherein the genetic variants include single nucleotide variants.

23. The method of claim 1 wherein the genetic variants include mutations.

24. The method of claim 1 wherein the genetic variants include point mutations.

25. The method of claim 1 wherein the genetic variant affects a single base.

26. The method of claim 24 wherein the genetic variant affects more than a single base.

27. The method of claim 1 wherein multiple test locations indicate the nature of the target sequence by the detection of genetic variants in the target sequence.

28. The method of claim 1 wherein distinguishable reporters at a single test site location indicate the nature of the target sequence by the detection of genetic variants in the target sequence.

29. The method of claim 1 wherein the plurality of hybridization complex assays form an array.

30. The method of claim 29 wherein the location of the test site in the array indicates the nature of the genetic variant.

31. The method of claim 1 wherein a test site is determined to be concordant when the hybridization complex present there is stable relative to other test sites for the same locus.

32. The method of claim 1 wherein the stability is enhanced by complementary match of bases in the hybridization complex including the capture, reporter and target.

33. The method of claim 1 wherein the hybridization complex assay is determined to be concordant when a distinguishable reporter present there is stable relative to other distinguishable reporters for the same locus.

34. The method of claim 1 wherein the base stacked pair is 5'GpC3'.

35. The method of claim 1 wherein the base stacked pair is 5'TpA3'.

36. The method of claim 1 further including modifications of terminal nucleotides which increase base stacking.

37. The method of claim 1 wherein stability is enhanced with ligation techniques.

38. The method of claim 1 wherein discordance includes a genetic variant.

39. The method of claim 38 wherein the genetic variant is in the target sequence.

40. The method of claim 38 wherein the genetic variant in the target sequence is selected from the group comprising: insertions, deletions, transitions and transversions.

41. The method of claim 1 wherein discordance includes genetic variations which are greater than a single nucleotide.

42. The method of claim 1 wherein the number of loci analyzed at one time is one.

43. The method of claim 1 wherein the number of loci analyzed at one time is three.

44. The method of claim 1 wherein the number of loci analyzed at one time is less than five.

45. The method of claim 1 wherein the number of loci analyzed at one time is less than ten.

46. The method of claim 1 wherein the number of loci analyzed at one time is greater than ten.

47. The method of claim 1 wherein the number of loci analyzed at one time is less than one hundred.

48. The method of claim 1 wherein the number of loci analyzed at one time is greater than one hundred.

49. The method of claim 1 wherein the disruption of the juxtaposed termini results in destabilization of the hybridization complex.

50. The method of claim 1 wherein the disruption of complementary sequences results in destabilization of the hybridization complex.

51. The method of claim 1 wherein the disruption of the juxtaposed termini and complementary sequences results in destabilization of the hybridization complex.

52. The method of claim 1 wherein the hybridization stability is determined, at least in part, by thermal regulation of stringency.

53. The method of claim 1 wherein the hybridization stability is determined, at least in part, by chemical regulation of stringency.

54. The method of claim 1 wherein initial hybridization step occurs in 10 minutes or less.

55. The method of claim 1 wherein initial hybridization step occurs in 5 minutes or less.

56. The method of claim 1 wherein initial hybridization step occurs in 1 minute or less.

57. The method of claim 1 wherein the hybridization complex is labeled.

58. The method of claim 57, further including the step of detecting the amounts of labeled hybridization complex at the test sites.

59. The method of claim 58 wherein the detecting is imaging.

60. The method of claim 59 wherein the imaging is optical imaging.

61. The method of claim 59 wherein the imaging is electronic imaging.

62. The method of claim 59 wherein the imaging is CCD imaging.

63. The method of claim 59 wherein the imaging is integrated optical imaging.

64. The method of claim 59 wherein the imaging detection is quantified.

65. The method of claim 1 further including a statistical analysis step.

66. The method of claim 1 wherein the labeled portion of complex is the target.

67. The method of claim 1 wherein the labeled portion of complex is the capture.

68. The method of claim 1 wherein the labeled portion of complex is the reporter.

69. The method of claim 1 wherein the labeling is by fluorescent labeling.

70. The method of claim 69 wherein the fluorescent labeling is with Bodipy Texas Red.

71. The method of claim 69 wherein the fluorescent labeling is with Bodipy 630/650.

72. The method of claim 69 wherein the fluorescent labeling is with Lucifer Yellow.

73. The method of claim 57 wherein the labeling is by colormetric labeling.

74. The method of claim 57 wherein the labeling is by chemiluminescent labeling.

75. The method of claim 1 further including energy transfer between molecules in the hybridization complex.

76. The method of claim 75 wherein the energy transfer includes quenching.

77. The method of claim 1 further including a redundant assay.

78. The method of claim 77 further including the step of repeating the redundant assay until a statistically significant result is obtained.

79. The method of claim 77 wherein the redundant assay includes multiple arrays.

80. The method of claim 1 wherein the target DNA is purified.

81. The method of claim 1 wherein the target is unamplified.

82. The method of claim 1 wherein the target is amplified.

83. The method of claim 1 wherein the target is applied to a reduction of test sites necessary to identify the number of repeat units in the target DNA.

84. The method of claim 83 wherein the reduction increases the statistical significance of results.

85. The method of claim 1 wherein the target material constitutes homozygous allele for a locus.

86. The method of claim 1 wherein the target material constitutes heterozygous allele for a locus.

87. The method of claim 1 wherein the target material constitutes more than one allele per locus for a mixed sample.

88. The method of claim 87 wherein the mixed sample further includes sample from more than one individual.

89. The method of claim 88 wherein the mixed sample further includes tumor tissue mixed with normal tissue.

90. The method of claim 1 wherein the capture probe and reporter probe are selected from a plurality of options by varying at least the position of the juxtaposed termini relative to the genetic variant.

91. The method of claim 1 wherein the genetic variant is at an end of the reporter probe.

92. The method of claim 1 wherein the genetic variant is at an end of the capture probe.

* * * * *